United States Patent
Fernandes et al.

(10) Patent No.: US 9,987,378 B2
(45) Date of Patent: Jun. 5, 2018

(54) PRUSSIAN BLUE-INSPIRED CONSTRUCTS FOR MULTIMODAL IMAGING AND THERAPY

(71) Applicant: Children's National Medical Center, Washington, DC (US)

(72) Inventors: Rohan Fernandes, Bethesda, MD (US); Matthieu F. Dumont, Tallahassee, FL (US); Raymond W. Sze, McLean, VA (US); Laurie S. Conklin, Columbia, MD (US); Hilary A. Hoffman, Lewisberg, WV (US); Jyoti K. Jaiswal, Rockville, MD (US)

(73) Assignee: Children's National Medical Center, Washington, DC (US)

( * ) Notice: Subject to any disclaimer, the term of this patent is extended or adjusted under 35 U.S.C. 154(b) by 0 days. days.

(21) Appl. No.: 15/390,106

(22) Filed: Dec. 23, 2016

(65) Prior Publication Data
US 2017/0173187 A1    Jun. 22, 2017

Related U.S. Application Data

(63) Continuation of application No. 14/213,380, filed on Mar. 14, 2014, now Pat. No. 9,561,183.

(60) Provisional application No. 61/794,156, filed on Mar. 15, 2013.

(51) Int. Cl.
| | |
|---|---|
| A61B 5/00 | (2006.01) |
| A61B 8/00 | (2006.01) |
| A61B 10/00 | (2006.01) |
| A61K 49/00 | (2006.01) |
| A61K 9/14 | (2006.01) |
| A61K 41/00 | (2006.01) |
| C01C 3/12 | (2006.01) |
| A61K 47/69 | (2017.01) |

(52) U.S. Cl.
CPC .......... *A61K 49/0032* (2013.01); *A61K 9/143* (2013.01); *A61K 41/0052* (2013.01); *A61K 47/6923* (2017.08); *C01C 3/12* (2013.01); *A61K 49/0017* (2013.01); *C01P 2004/04* (2013.01)

(58) Field of Classification Search
None
See application file for complete search history.

(56) References Cited

U.S. PATENT DOCUMENTS

| 7,687,188 B2 | 3/2010 | Marubayashi et al. |
|---|---|---|
| 8,092,783 B2 | 1/2012 | Huang et al. |
| 9,561,183 B2 * | 2/2017 | Fernandes .............. A61K 9/143 |
| 2010/0215587 A1 | 2/2010 | Huang |
| 2010/0254912 A1 | 10/2010 | Huang et al. |

FOREIGN PATENT DOCUMENTS

| EP | 1 208 005 | 5/2002 |
|---|---|---|
| WO | 2008/127019 | 10/2008 |
| WO | 2012/108856 | 8/2012 |
| WO | 2012/110835 | 8/2012 |

OTHER PUBLICATIONS

J. Xie et al., "Nanoparticle-based theranostic agents," Advanced Drug Delivery Reviews, 2010, 62, 1064-1079.
Radiogardase® drug label can be found at (using Radiogardase or Prussian blue in drug search box):—http://www.accessdata.fda.gov/scripts/cder/drugsatfda/index.cfm.
Viktória Hornok et al., "Synthesis and stabilization of Prussian blue nanoparticles and applications for sensors," Journal of Colloid and Interface Science, 2007, 309, 176-182.
Mohammadreza Shokouhimehr et al., "Biocompatible Prussian blue nanoparticles: Preparation, stability, cytotoxicity and potential use as an MRI contrast agent," Inorganic Chemistry Communications, 2010, 13, 58-61.
Mohammadreza Shokouhimehr et al., "Dual purpose Prussian blue nanoparticles for cellular imaging and drug delivery: a new generation of T1-weighted MRI contrast and small molecule delivery agents," Journal of Materials Chemistry, 2010, 20, 5251-5259.
Mohammadreza Shokouhimehr et al., "Prussian blue nanoparticles and its analogues as new-generation T1-weighted MRI contrast agents for cellular imaging," Thesis submitted to Kent State University, 2010, 93 pages.
Matthieu F. Dumont et al., "Biofunctionalized Gadolinium-Containing Prussia Blue Nanoparticles as Multimodal Molecular Imaging Agents", Bioconjugate Chemistry, 2013, 9 pages.
International Search Report and the Written Opinion dated Aug. 20, 2014, in International Application No. PCT/US2014/031045 (with Search History).

(Continued)

*Primary Examiner* — Michael G Hartley
*Assistant Examiner* — Melissa J Perreira
(74) *Attorney, Agent, or Firm* — Oblon, McClelland, Maier & Neustadt, L.L.P.

(57) ABSTRACT

The invention describes a coordination polymer construct for multimodal imaging and therapy. The construct consists of a core particle made of a novel coordination polymer. The core is coated with a biocompatible coating that stabilizes the particles in a physiological environment. The biocompatible coating can contain attached targeting agents, imaging agents and therapeutic agents or combinations one or more of the targeting, imaging and therapeutic agents. When administered to a subject or a subject-derived specimen, the resulting coordination polymer core-shell construct enables multimodal imaging and therapy, which improves the diagnostic and treatment outcomes of the conditions or diseases where it is administered. The invention describes the novel material, base for the construct, methods for the preparation of the said construct and its use as a multimodal imaging and therapy agent.

13 Claims, 24 Drawing Sheets

(56) References Cited

OTHER PUBLICATIONS

Matthieu Francois Dumont, "Nanostructures of Metallophosphates and Cyanometallates for Applications and Physical Studies", University of Florida, 2011, 196 pages, Retrieved form the internet:URL:http://etd/fcla.edu/UF/UFE0042791/dumont_m.pdf.
Pooja M. Tiwari, et al., "Functionalized Gold Nanoparticles and Their Biomedical Applications", Nanomaterials, ISSN 2079-4991, vol. 1, 2011, pp. 31-63, Retrieved form the internet:URL:http://www.google.com/url?sa=t&rct=J&q=&esrc=s&source=web&cd=2&ved=0CDEQFjAB&url=http%3A%2F%2Fwww.mdpi.com%2F2079-4991%2F1%2F1%2F31%2Fpdf&ei=K17NU-nEKdafyATTvYGIDQ&usg=AFQjCNErx8WSRHovxpbFmdBM3AQMsRySQA&sig2=ShTy6Vis_7mTRjkeOtiJHg&bvm=bv.71198958,d.aWw>.
Pajerowski et al. (J. Am. Chem. Soc. 2009, 131, 12927-12936).
Zhuo et al. (Biomaterials 2009, 30, 2284-2290).

\* cited by examiner

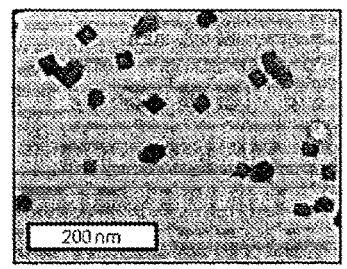
Figure 20A
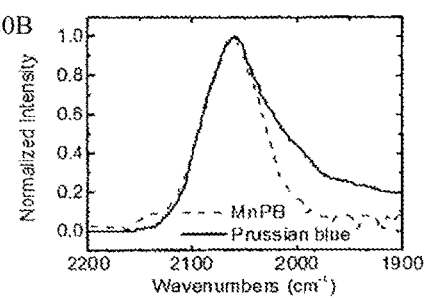
Figure 20B
Figure 21
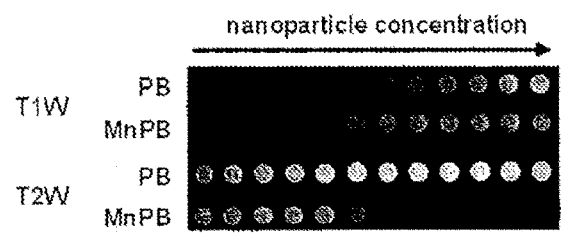
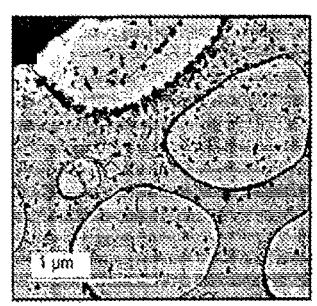
Figure 22A
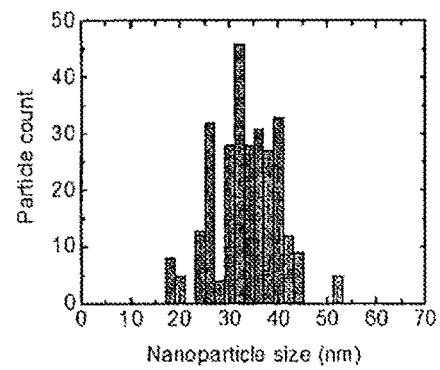
Figure 22B Fig. 23
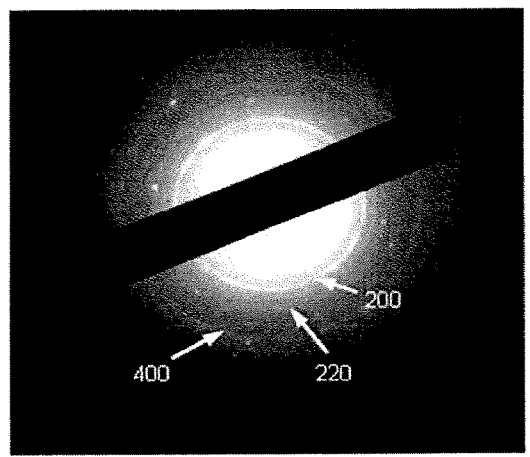
Fig. 24A     Fig. 24B
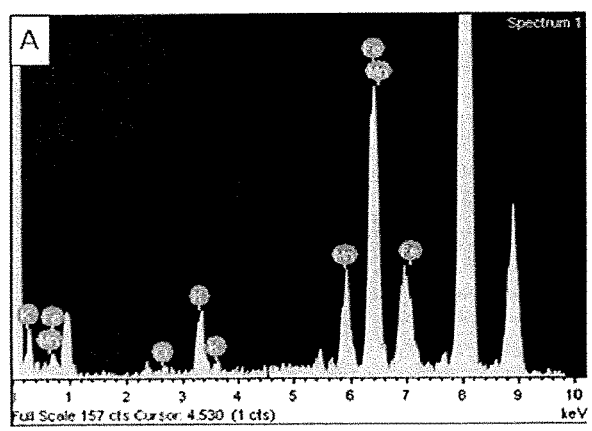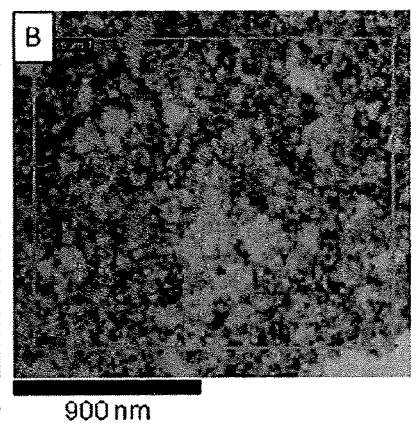

Fig.31A                Fig. 31B                Fig. 31C
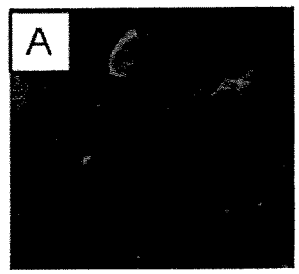  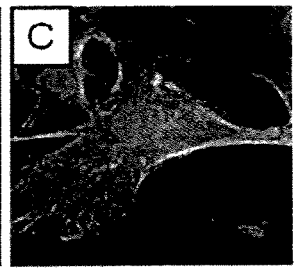
Fig. 32A
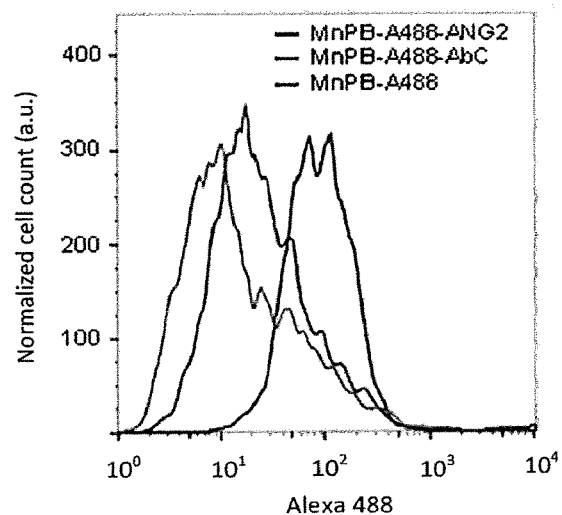
Fig. 32B
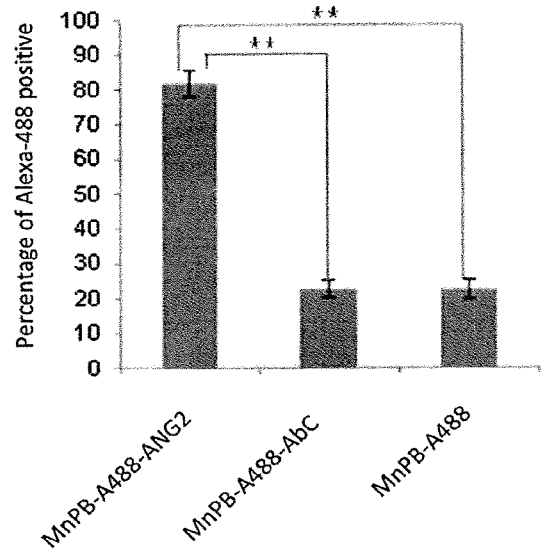

Figure 33A, 33B, and 33C
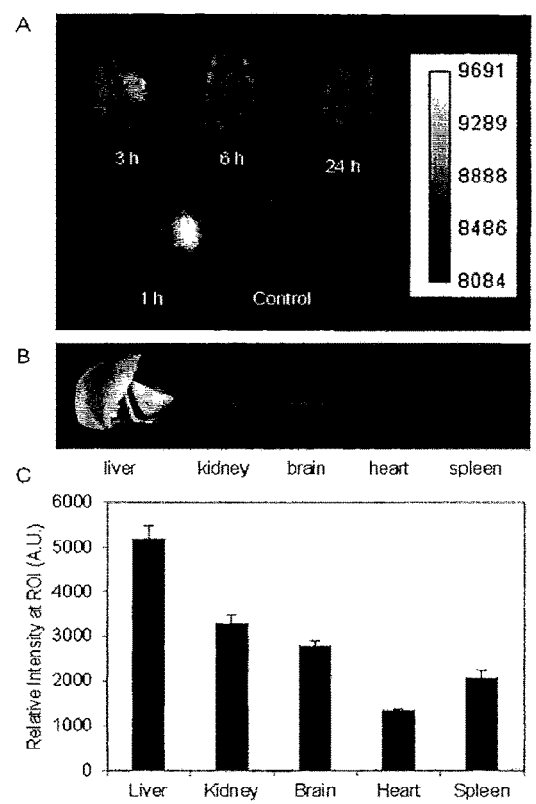

Figure 34A, 34B, 34C, and 34D
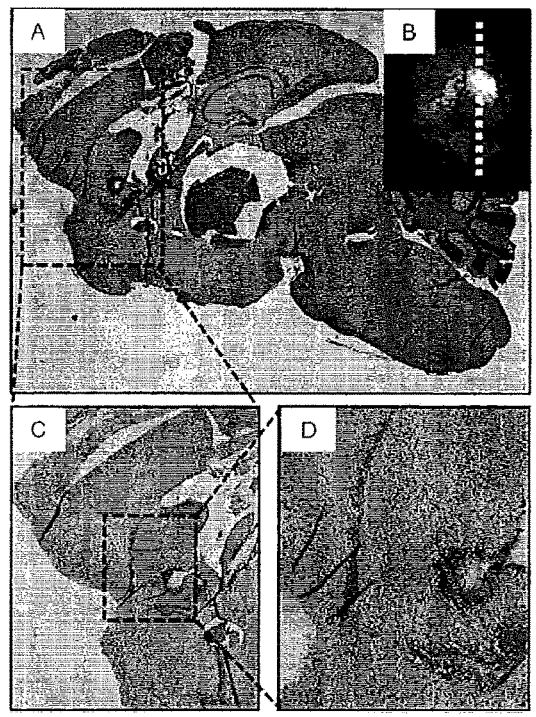
Figure 35
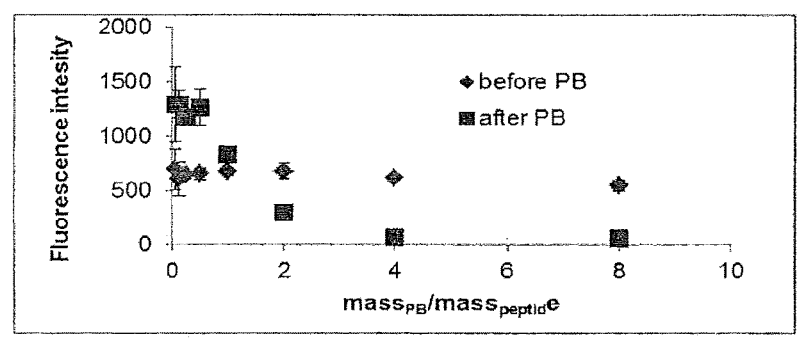

PRUSSIAN BLUE-INSPIRED CONSTRUCTS FOR MULTIMODAL IMAGING AND THERAPY

CROSS REFERENCE TO RELATED APPLICATION

This application claims the benefit of U.S. Provisional Application No. 61/794,156, filed on Mar. 15, 2013, the entire disclosure thereof is incorporated herein by reference.

FIELD OF THE INVENTION

The present invention is in the field of theranostics. The invention describes a material that can be used as MRI contrast agent and its preparation. Further, the invention describes biofunctionalization of the construct and subsequent addition of targeting, imaging and/or therapeutic molecules or particles. The invention also describes procedures relating to multimodal imaging and therapy agents.

BACKGROUND OF THE INVENTION

Thernanostic agents are agents that can simultaneously perform therapy and diagnostics using a single platform. Theranostic agents are typically nanoparticles or microparticles with additional functionalities that confer both diagnostic and therapeutic capabilities to the agent. A variety of particle-based theranostic agents have been described (Xie et al., 2010) including, iron oxide, gold, quantum dot, carbon nanotube and silica particle-based theranostic agents. Here we describe a coordination polymer, particle-based theranostic agents.

Coordination polymers having their general structure involving a network of metal ions linked orthogonally by cyanide bridges are commonly referred as Prussian blue analogs or belonging to the Prussian blue family. Prussian blue is a synthetic dye that was synthesized in the early 18th century. Chemically, Prussian blue is iron (III) hexacyanoferrate (II) and exists in two forms—a "soluble" form that can be stably dispersed as a colloid in water (though it is insoluble in water) with a structural formula $KFe_3[Fe(CN)_6]$ and an "insoluble" form with a structural formula $Fe_4[Fe(CN)_6]$, that cannot be stably dispersed as a colloid in water. The insoluble form of Prussian blue $Fe_4[Fe(CN)_6]$ is sold as an FDA approved drug RADIOGARDASE® by Heyltex Corporation (RADIOGARDASE® drug label; FDA website). Radiogardase contains 0.5 grams of insoluble Prussian blue powder in gelatin capsules containing 0-38 mg of microcrystalline cellulose. It is used for treating patients who are suspected or known to have internal contamination with radioactive/non-radioactive thallium or radioactive cesium to increase the elimination rates of the said elements from the body of treated patients.

Most forms of coordination polymers belonging to the Prussian blue family have a high affinity for cations, which they mechanically trap, adsorb or sequester via cation exchange. This ion sequestration ability of especially the "soluble" form of Prussian blue has been tapped by various groups to synthesize medical contrast agents. Methods have been described to synthesize Prussian blue nanoparticles and their use as MRI contrast agents in the literature (Hornok and Dekany, 2007; Shokouhimehr et al, 2010a, 2010b, 2010c, Huang SP 2010, 2012). Kawamoto et al. in U.S. Pat. No. 7,687,188 B2 disclose a method for producing ultrafine particles of a Prussian blue-type metal complex but do not describe in specific imaging uses. Huang et al. in U.S. Pat. No. 8,092,783 B2 describe gadolinium containing Prussian blue nanoparticles for use as a non-toxic MRI contrast agent but they do not describe other imaging or therapeutic uses for the gadolinium containing Prussian blue nanoparticles. Mathe et al. in WO/2012/110835 describe Prussian blue based nanoparticles with a generalized structure $A_xN'_n[M(CN)_6]$ surrounded by metal isotopes and an organic biocompatible coating. Further, they describe the use of their said agent for multimodal imaging, cancer cell and tumor detection and therapy.

Described herein are novel compounds having a Prussian blue analog lattice compound represented by a generalized structural formula $A_xB_yM_4[M'(CN)_6]_z \cdot nH_2O$ and the synthesis thereof. The incorporation of elements B within the Prussian blue-type lattice along with the water molecules of the core, provide surprisingly superior imaging capabilities than the constructs described above.

BRIEF SUMMARY OF THE INVENTION

One object of the present invention is to provide a composition, comprising a core of doped Prussian blue analog lattice compound comprising interstitial cations and a shell of biocompatible coating modified with a fluorophore, a contrast agent, a targeting agent, a therapeutic agent, or any combination thereof.

In one embodiment of the present invention, the Prussian blue analog lattice compound is a compound represented by generalized formula (I):

$$A_xB_yM_4[M'(CN)_6]_z \cdot nH_2O \qquad (I).$$

wherein:

A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

B represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M' represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

x is from 0.1 to about 1;
y is from 0.1 to about 1;
z is from 0.1 to about 4; and
n is from 0.1 to about 24.

A further embodiment is the biofunctionalization and specifics about its modifications with targeting, imaging or therapeutic agents. Finally, further embodiment is its use for multimodal imaging and therapeutic purposes. The new material comprises a coordination polymer. The core is surrounded with a biocompatible coating onto which targeting, imaging and therapeutic agents, or combinations thereof, are attached. The constructs comprising the coordination polymer core and its biofunctional shell can be used for multimodal imaging including cancer cell and tumor sensing, medical radiography, magnetic resonance imaging, scintigraphy, X-ray computed tomography, single-photon emission computed tomography, positron emission tomography, photoacoustic imaging, ultrasound imaging, near infrared imaging, optical imaging and fluorescence imaging, and for therapy.

BRIEF DESCRIPTION OF THE DRAWINGS

FIGS. 20A and 20B show the physical and chemical characterization of the MnPB nanoparticles.

FIG. 21 shows a T1 and T2 weighted MR images at 3 T showing hyper and hypointensity from PB and MnPB.

FIGS. 22A and 22B show the size of the MnPB nanoparticles.

FIG. 23 shows a SAED pattern for MnPB.

FIGS. 24A and 24B show images relating to the composition of MnPB.

FIGS. 31A, 31B, and 31C show the fluorescence-based detection of PBT cells using the biofunctionalized Prussian blue nanoparticles.

FIGS. 32A and 32B show the flow cytometric analysis of the specificity of the biofunctionalized MnPB for PBT cells.

FIGS. 33A, 33B, and 33C show ex vivo fluorescence imaging of nanoparticles in an orthotopic mouse model of PBTs.

FIGS. 34A, 34B, 34C, and 34D show a histological analysis of the fluorescence positive regions of the mice brains with PBTs.

FIG. 35 shows a value of the fluorescence intensity of Cy5.5 before and after addition of variable amount of quenching coordination polymer particle.

FIG. 37 show results for mice from Group 1, Group 2, and Group 3 after 8 days post-treatment (Top). Tumors from each group were extracted, sectioned, and stained with H&E (Bottom).

DETAILED DESCRIPTION OF THE INVENTION

Figure 1:
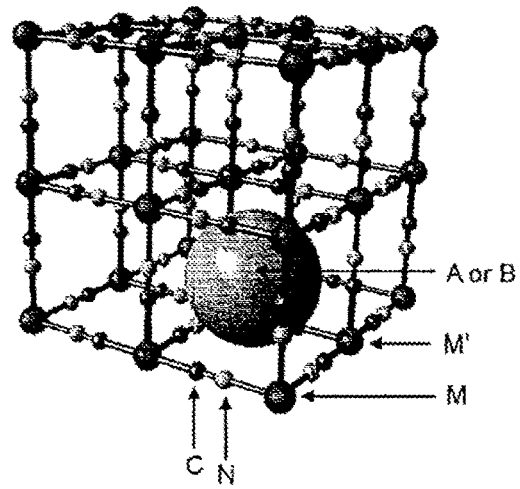
FIG. 1 shows a graphical representation of the component metals A, B, M and M' and elements C and N that are used in the synthesis of the Coordination polymer core

Unless indicated otherwise, the symbols used to represent the elements of which the Prussian blue analog lattice compound of the present invention are comprised are the symbols used in the periodic table of elements to represent the chemical elements (for example, "Fe" represents iron, etc.). In addition, unless indicated otherwise, the indefinite articles "a" and "an" are synonymous with "at least one" or "one or more." Unless otherwise indicated, the terms "coordination polymer" and "Prussian blue analog lattice compound" used herein are synonymous.

Terms used herein such as "comprising," "consisting essentially of," and "consisting of" have their ordinary and customary meaning under U.S. patent law. Unless otherwise indicated, the transitional term "comprising" is synonymous with "including," "containing," or "characterized by" and is inclusive or open-ended and does not exclude additional, unrecited elements or method stages. Unless otherwise indicated, the transitional term "consisting essentially of" limits the scope of the claim to the materials specified and/or recited in the body of the claim or method stages specified and/or recited in the body of the claim, and this transitional phrase excludes those materials or stages that do not materially affect the basic and novel characteristics of the claimed invention. Unless otherwise indicated, the transitional term "consisting of" limits the scope of the claim to only those materials specified and/or recited in the body of the claim or to only those method stages specified and/or recited in the body of the claim.

Unless indicated otherwise, the terms "contrast agent" and "imaging agent" used herein can be used interchangeably.

Embodiment 1: Novel Material

A first embodiment of the invention is a composition of a Prussian blue analog lattice compound represented by general formula (I):

$$A_xB_yM_4[M'(CN)_6]_z \cdot nH_2O \quad (I),$$

which is coated with a biocompatible shell onto which targeting, imaging and/or therapeutic agents are attached. In the compounds of general formula (I), A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof; B represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof; M represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof; M' represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof; x is from 0.1 to about 1; y is from 0.1 to about 1; z is from 0.1 to about 4; and n is from 0.1 to about 24.

In preferred embodiments, A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and in any combination thereof.

In the further preferred embodiments, A represents at least one of Li, Na, K, Rb, Cs, and Fr, in any oxidation state and in any combination thereof. In other preferred embodiments, A represents Li, Na, K, Rb, in any oxidation state and in any combination thereof. In other preferred embodiments, A represents a mixture of K and other elements represented by A, where the molar ratio of K in the mixtures is at least 0.9, preferably, at least 0.95, most preferably at least 0.99. In the most preferred embodiments, A only represents K.

In preferred embodiments, B represents at least one of Cr, Mn, Fe, Eu, Gd, and Tb, in any oxidation state and in any combination thereof. In other preferred embodiments, B represents a mixture of Mn, Gd, and other elements represented by A, where the molar ratio of the combination of Mn and Gd in the mixtures is at least 0.9, preferably, at least 0.95, most preferably at least 0.99. In the most preferred embodiments, A represents a mixture of only Mn and Gd, in any oxidation state and in any combination thereof.

In preferred embodiments, M represents at least one of Fe, Co, and Ni, in any oxidation state and in any combination thereof. In the most preferred embodiments, M represents only Fe.

In preferred embodiments, M' represents at least one of Fe, Co, and Ni, in any oxidation state and in any combination thereof. In the most preferred embodiments, M' represents only Fe.

In the most preferred embodiments, each of M and M', simultaneously, represents only Fe, in any oxidation state thereof.

As used herein, the term "in any combination thereof" for A, B, M, and M' means that at least two of the elements that are represented by A, B, M, and M' can be present in any molar ratios so long as the sum total is equal to the value for x, y, and z, and, in the case of M, the elements can be present in any molar ratios so long as the total amount of the M elements is equal to 4.

Preferably, x in general formula (I) is from 0.2 to 0.9, more preferably from 0.3 to 0.8, more preferably still from 0.4 to 0.7, and most preferably from 0.5 to 0.6. Preferably, y in general formula (I) is from 0.2 to 0.9, more preferably from 0.3 to 0.8, more preferably still from 0.4 to 0.7, and most preferably from 0.5 to 0.6. Preferably, z in general formula (I) is from 0.2 to 3.5, more preferably from 0.3 to 0.8, more preferably still from 0.4 to 0.7, and most preferably from 0.5 to 0.6. All real numbers within the ranges for x, y, z, and n are included.

Particularly preferred species of the Prussian blue analog lattice compound represented by general formula (I) are $K_{0.53}Gd_{0.89}Fe^{III}_4[Fe^{II}(CN)_6]_{3.8} \cdot 1.2H_2O$ and $K_{0.6}Mn_{0.7}Fe^{III}_4[Fe^{II}(CN)_6]_{3.5} \cdot 3H_2O$.

FIG. 1 illustrates a representative lattice structure of a Prussian blue analog lattice compound, where M, M', C, N, A and/or B atoms are shown in the lattice.

In other preferred embodiments of the present invention, the doped Prussian blue analog lattice compounds according to the invention have particle sizes of about 1 nanometer (nm) to about 10 microns (μm). Preferably, the particle sizes are from 5 nm to 5 microns, and more preferably from 10 nm to 1 micron. As used herein, the term "micron" is synonymous with "micrometer." Further, the units of length herein are those defined according to the International system of units ("SI units"), where a micron is $1\times10^{-6}$, a nanometer is $1\times10^{-9}$, etc.

In embodiments of the present invention, the doped Prussian blue analog lattice compounds represented by general formula (I) are synthesized by a method comprising, consisting essentially of, or consisting of reacting a metallic salt with a metal cyanide ($[M'(CN)_6]^{3-}$) in a solvent, the solvent further comprising a polymer or a compound comprising $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho in any oxidation state and any combination thereof. In these methods, the metallic salt comprises, consists essentially of, or consists of a salt of salt of V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho in any oxidation state thereof and in any combination thereof. In preferred embodiments, the metallic salt comprises, consists essentially of, or consists of a metallic salt of a chloride, a nitrate, a nitrite, a sulfate, a fluorinate, a glutamate, an acetate, a carbonate, a citrate, a phosphate, a sulfate and any combination thereof. In preferred embodiments, the metal cyanide comprises, consists essentially of, or consists of a metal cyanide represented by $[M'(CN)_6]^{3-}$, wherein M' represents V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho in any oxidation state thereof and in any combination thereof.

The solvent in which the reaction between the metallic salt and the metallic cyanide described above occurs is not particularly limited, so long as the reaction proceeds in this solvent. Preferably, the solvent comprises, consists essentially of, or consists of water, air, or an organic solvent. The organic solvent can be hydrophilic to any degree or hydrophobic to any degree. Preferably, the organic solvent comprises, consists essentially of, or consists of hexane; benzene; toluene; diethyl ether; chloroform; 1,4-dioxane; ethyl acetate; tetrahydrofuran (THF); dichloromethane; acetone; acetonitrile (MeCN); dimethylformamide (DMF); dimethyl sulfoxide (DMSO); a polar protic solvent; acetic acid; n-butanol; isopropanol; n-propanol; ethanol; methanol; formic acid; and any combination thereof, so long as the metallic salt and the metallic cyanide are sufficiently dissolved in the combination and the reaction proceeds in this combination of solvents.

The polymer that can be present in the mixture in which the reaction proceeds is not particularly limited, so long as the polymer is sufficiently compatible with the solvent, the metallic salt, and the metallic cyanide and the reaction proceeds. In preferred embodiments, the polymer comprises, consists essentially of, or consists of ADOGEN® 464, ALKANOL® 6112, BRIJ® 52, BRIJ® 93, BRIJ® S2, BRIJ® S, BRIJ® L4, BRIJ® 010, BRIJ® S10, BRIJ® S20, Ethylenediamine tetrakis(ethoxylate-block-propoxylate) tetrol, IGEPAL® CA-210, IGEPAL® CA-520, IGEPAL® CA-720, IGEPAL® CO-630, IGEPAL® CO-890, IGEPAL® DM-970, MERPOL® DA, MERPOL® HCS, MERPOL® OJ, MERPOL® SE, MERPOL® SH, MERPOL® A, poly(ethylene glycol) sorbitan tetraoleate, poly(ethylene glycol) sorbitol hexaoleate, poly(ethylene glycol), polyethylene-block-poly(ethylene glycol), sorbitan monopalmitate, 2,4,7,9-tetramethyl-5-decyne-4,7-diol ethoxylate, 2,4,7,9-tetramethyl-5-decyne-4,7-diol, TRITON™ N-101, TRITON™ X-100, TRITON™ X-100 reduced, TRITON™ X-114, TRITON™ X-405, reduced, TWEEN® 20, TWEEN® 40, TWEEN® 60, TWEEN® 85, ZONYL® FS-300, ZONYL® FSA, ZONYL® FSN, ZONYL® FSO fluorosurfactant, acrylic acid (AA), 4,4'-azobis(4-cyanopentanoic acid); ACPA), 2,2'-azobisisobutyronitrile (AIBN), sodium bis(2-ethylhexyl) sulfosuccinate (AOT), sodium dihexyl sulfosuccinate (AMA-80), Amphi-Dex, acrylonitrile (AN), bis(2-pyridylmethyl)-octadecylamine (BPMODA), BRIJ® 30 (polyoxyethylene-4-lauryl ether), 1-butyl-3-methylimidazolium hexafluorophosphate ([C4mim]PF6), poly(oxyethylene) octyl phenyl ether (CA897),CMC-A9, carboxymethylated poly(ethylene glycol) (CMPEG), cetyltrimethylammonium bromide (CTAB), cetyltrimethylammonium chloride (CTMA-Cl), didodecyldimethylammonium bromide (DDAB), dodecanoic acid 2-(2-hydroxyethoxy)ethyl ester (DDA-HEEE), decyltrimethylammonioumbromide (DeTAB), dodecyl mercaptane (DDM), dextran ester (DexEst), SG1-based difunctional alkoxyamine (DIAMA-Na), dimethyl acetamide (DMAc), dodecyl methacrylate (DMA), (dimethylamino)ethyl methacrylate (DMAEMA), 3-(N,N-dimethylmyristylammonio) (DMMA-PS), dodecyl mercaptane, dodecyltrimethylammonioumbromide (DTAB), methacrylic acid copolymer (EUDRAGIT® L100-55), poly(ethylene-co-butylene)-b-poly(ethylene oxide) (KLE3729), lauryl methacrylate (LMA), monomethoxy-poly(ethylene glycol) (mPEG), monomethoxy-poly(ethylene oxide)-poly(lactic acid) (mPEO-PLA), methyl methacrylate (MMA), octyl trimethyl ammonium bromide (OTAB), polyaniline-poly(styrenesulfonic acid) (PANI-PSS), poly(γ-benzyl-l-glutamate)-b-poly(ethylene oxide) (PBG-PEO), poly(ε-caprolactum) (PCL), poly(oxyethylene)-poly(oxypropylene) copolymer (PE/F68), poly(ethylene oxide) (PEO), poly(ethyleneglycol) (PEG), poly(hydroxyl butyrate) (PHB), poly(heptadecafluorodecylacrylate) (PHDFDA), poly(hydroxyethyl methacrylate) (PHEMA), poly(lactide-fumarate) (PLAF), poly(d,l-lactic acid-co-glycolic acid) (PLGA), poly(lactide-co-glycolide fumarate) (PLGF), poly(l-lactic acid) (PLLA), Pluronic F-108, poly(α,β-l-malic acid) (PMA), poly(methyl methacrylate) (PMMA), poly(N-isopropylacrylamide-co-methacrylic acid) (P(NIPAM-MAA)), poly(ethylene oxide)-poly(propylene oxide) ethylene diamine copolymer(Poloxamine 908), poly(styrenesulfonic acid) (PSS), poly(trimethylene carbonate) (PTMC), poly(vinyl alcohol) (PVA), sodium 4-(v-acryloyloxyalkyl) oxy benzene sulfonate (SABS), sodium dodecyl sulfate (SDS), sodium lauryl sulfate (SLS), sodiumoctylbenzene sulfonate (SOBS), stearyl methacrylate (SMA), 5-sulfoisophthalic acid dimethyl ester sodium salt modified tetracarboxylic acid-terminated polyester (SMTAPE), sorbitan monopalmitate (SPAN® 40), sorbitan monooleate (SPAN® 80), sorbitane trioleate (SPAN® 85), sodium persulfate (SPS).

In preferred embodiments of the invention, the reaction between the metallic salt and the cyanometallate in the mixture can be carried out by mixing these reactants by magnetic stirring, mechanical stirring, slow diffusion, ball-milling, sonication, or a combination thereof.

The temperature at which the reaction between the metallic salt and the metallic cyanide is conducted is not particularly limited, so long as the reaction occurs. In preferred embodiments, the reaction is carried out at a temperature ranging from 0 to 100° C., preferably from 25 to 75° C. All real numbers within these ranges are included. Further, the temperature can be increased or decreased during the reaction at any rate and at any number of times, provided that the reaction proceeds.

Embodiment 2: Biocompatibility and Biomarker Targeting

Figure 2:
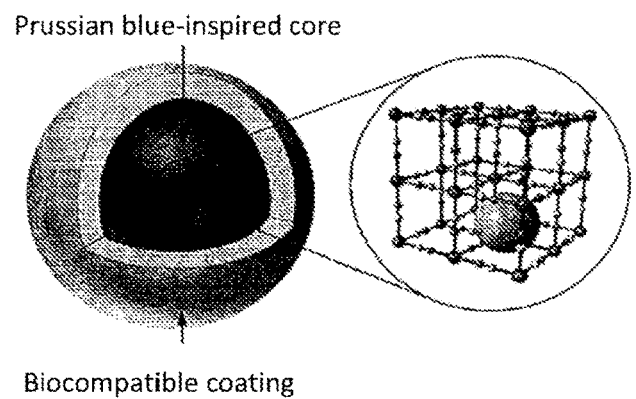
FIG. 2 shows a graphical representation of the biocompatible coating of the coordination polymer core. The coating surrounds the core and serves multiple purposes as described in the invention.

Another object of the present invention is to provide a composition that comprises, consists essentially of, or consists of a core surrounded by and in contact with a biocompatible shell. A representative, non-limiting illustration of a core-shell type composition according to this embodiment is shown in FIG. 2, where a Prussian blue analog lattice compound represented by general formula (I) is shown to be encompassed by a biocompatible coating.

The core comprises, consists essentially of, or consists of the Prussian blue analog lattice compound represented by general formula (I) described above. The biocompatible shell comprises, consists essentially of, or consists of at least one material selected from the group consisting of dextran; chitosan; silica; polyethylene glycol (PEG); avidin; a proteins; a nucleic acids; a carbohydrates; a lipid; neutravidin; streptavidin; gelatin; collagen; fibronectin; albumin; a serum protein; lysozyme; a phospholipid; a polyvinyl pyrrolidone (PVP); a polyvinyl alcohol; a polyethylene glycol diacrylate; and a combination thereof. Without wishing to be bound to any particular theory, the biocompatible coating is believed to prevent the compositions from aggregating and to prevent leakage of ions from the core to the surrounding environment. The biocompatible coating can be applied to the core by a variety of physical and chemical interactions including but not limited to electrostatic (charge-based), covalent, hydrophobic and van der Waal's interactions.

In preferred embodiments, the biocompatible coating comprises, consists essentially of, or consists of at least one member selected from the group consisting of dextran; chitosan; silica; polyethylene glycol (PEG); avidin; a protein; a nucleic acids; a carbohydrates; a lipid; neutravidin; streptavidin; gelatin; collagen; fibronectin; albumin; a serum protein; lysozyme; a phospholipid; a polyvinyl pyrrolidone (PVP); a polyvinyl alcohol; polyethylene glycol diacrylate; and combinations of the above.

In preferred embodiments, the dextran of the biocompatible coating comprises, consists essentially of, or consists of a dextran that is a complex, branched polysaccharide having chains of varying lengths, preferably chains having lengths of from about 3 to about 2000 kDa.

In preferred embodiments, the chitosan of the biocompatible coating comprises, consists essentially of, or consists of a linear polysaccharide having randomly distributed units of β-(1-4)-linked D-glucosamine (deacetylated unit) and units of N-acetyl-D-glucosamine (acetylated unit).

In preferred embodiments, the silica of the biocompatible coating comprises, consists essentially of, or consists of an oxide of silicon with the chemical formula $SiO_2$.

In preferred embodiments, the polyethylene glycol (PEG) of the biocompatible coating comprises, consists essentially of, or consists of polyethylene oxide (PEO) or polyoxyethylene oxide (POE).

In preferred embodiments, the avidin of the biocompatible coating comprises, consists essentially of, or consists of a protein produced in the oviducts of birds, reptiles and amphibians deposited in the whites of their eggs.

In preferred embodiments, the proteins of the biocompatible coating comprises, consists essentially of, or consists of are biological molecules comprises at least one chain of an amino acid.

In preferred embodiments, the nucleic acids of the biocompatible coating comprises, consists essentially of, or consists of DNA (deoxyribonucleic acid) and RNA (ribonucleic acid), peptide nucleic acid, morpholino-nucleic acid, locked nucleic acid, glycol nucleic acid, and threose nucleic acid.

In preferred embodiments, the carbohydrates of the biocompatible coating comprise, consist essentially of, or consist of a monosaccharide, a disaccharide, and oligosaccharide, and a polysaccharide.

In preferred embodiments, the neutravidin of the biocompatible coating comprises, consists essentially of, or consists of a deglycosylated (carbohydrate removed) variety of avidin.

In preferred embodiments, the streptavidin of the biocompatible coating comprises, consists essentially of, or consists of protein extracted from the bacterium *Streptomyces avidinii*.

In preferred embodiments, the collagen of the biocompatible coating comprises, consists essentially of, or consists of a protein having chains of amino acids organized in a triple helix. In other preferred embodiments, the collagen of the biocompatible coating comprises, consists essentially of, or consists of a protein having chains of amino acids in the form of a triple helix.

In preferred embodiments, the gelatin of the biocompatible coating comprises, consists essentially of, or consists of a substance derived from hydrolyzed collagen.

In preferred embodiments, the fibronectin of the biocompatible coating comprises, consists essentially of, or consists of a glycoprotein dimer comprising two polypeptide chains tethered by a disulfide bond.

In preferred embodiments, the albumin of the biocompatible coating comprises, consists essentially of, or consists of bovine serum albumin (BSA, fraction V), human serum albumin (HSA) and all serum albumin derived from mammals.

In preferred embodiments, the serum proteins of the biocompatible coating comprises, consists essentially of, or consists of at least one member selected from the group consisting of Orosomucoid; antitrypsin; alpha-1 antichymotrypsin; alpha-2 macroglobulin (AMG); haptoglobin; transferrin; beta lipoprotein (LDL); immunoglobulin A (IgA); immunoglobulin M (IgM); immunoglobulin G (IgG); immunoglobulin E (IgE); and immunoglobulin D (IgD).

In preferred embodiments, the lysozyme of the biocompatible coating comprises, consists essentially of, or consists of N-acetylmuramide glycanhydrolase.

In preferred embodiments, the phospholipids of the biocompatible coating comprise, consist essentially of, or consist of all natural phospholipids and synthetic phospholipids. Non-limiting examples of natural phospholipids and synthetic phospholipids include DMPA, DPPA, DSPA DDPC, DLPC, DMPC, DPPC, DSPC, DOPC, POPC, DEPC DMPG, DPPG, DSPG, POPG DMPE, DPPE, DSPE DOPE DOPS mPEG-phospholipid, polyglycerin-phospholipid, functionalized-phospholipid, and terminal activated-phospholipid.

In preferred embodiments, the polyvinyl pyrrolidone (PVP) of the biocompatible coating comprises, consists essentially of, or consists of a polymer made from repeating monomer N-vinylpyrrolidone units. The molecular weight of the PVP is not particularly limited, as long as the PVP is suitable for use in the biocompatible coating of the present invention. Other names for PVP are polyvidone and povidone.

In preferred embodiments, the polyvinyl alcohol of the biocompatible coating comprises, consists essentially of, or consists of PVOH, PVA, and PVAI. The molecular weights of the PVOH, PVA, and PVAI are not particularly limited, as long as the PVOH, PVA, and PVAI are suitable for use in the biocompatible coating of the present invention.

In preferred embodiments, the polyethylene glycol diacrylate of the biocompatible coating comprises, consists essentially of, or consists of a polyethylene glycol terminated with acrylate groups. The molecular weight of the polyethylene glycol diacrylate is not particularly limited, as long as the polyethylene glycol diacrylate is suitable for use in the biocompatible coating of the present invention.

In preferred embodiments, the lipids of the biocompatible coating comprises, consists essentially of, or consists of sterols, fats, oils, waxes, vitamin A, vitamin D, vitamin E, vitamin K, phospholipids of claim 5q, (mono-,di-,tri-) glycerides.

Embodiment 3: Imaging

Figure 3:
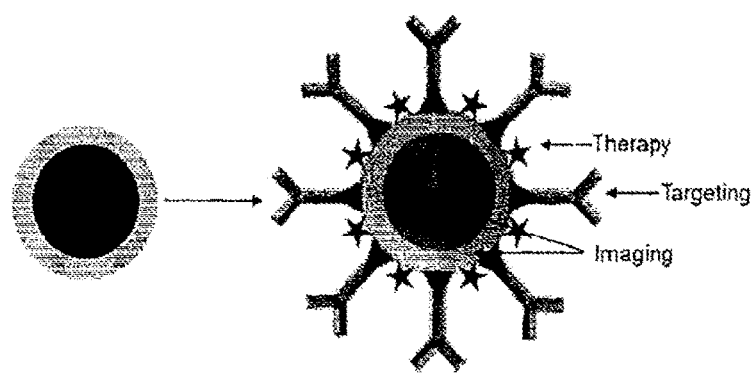
FIG. 3 shows a graphical representation of the targeting, imaging and therapy agents that are attached to the biocompatible coating or contained within it that enables multimodal imaging and therapy

In another embodiment of the invention, the core further comprises a targeting agent, imaging agent, a therapeutic agent, or a combination thereof. FIG. 3 represents a non-limiting example of a Prussian blue analog lattice compound bound to a targeting agent, a imaging agent, therapeutic agent, or a combination thereof.

Non-limiting examples of the targeting agent includes an antibody, a peptide, a protein, a nucleic acid, a carbohydrate, an aptamer, a small molecule, a synthetic molecule, and a combination thereof. Without wishing to be bound to a particular theory, the imaging agents are believed to facilitate medical radiography, magnetic resonance imaging, scintigraphy, X-ray computed tomography, single-photon emission computed tomography, positron emission tomography, photoacoustic imaging, ultrasound imaging, near infrared imaging, optical imaging and fluorescence imaging or combinations thereof and can be selected from the group consisting of a fluorophore, an imaging agent, a contrast agent, and a combination thereof.

In preferred embodiments, the fluorophore coating comprises, consists essentially of, or consists of a fluorescein compound, a rhodamine compound, a xanthene compound, a cyanine compound, a naphthalene compound, a coumarin compound, an oxadiazole compound, a pyrene compound, an oxazine compound, an acridine compound, an arylmethine compound, a tetrapyrrole compound, and proprietary molecules.

Non-limiting examples of the xanthene compound include fluorescein, rhodamine, Oregon green, eosin, Texas red, and naphthalene compounds such as dansyl and prodan compounds.

Non-limiting examples of the cyanine compound include cyanine, indocarbocyanine, oxacarbocyanine, thiacarbocyanine, and merocyanine.

Non-limiting examples of the oxadiazole compound include pyridyloxazole, nitrobenzoxadiazole and benzoxadiazole.

Non-limiting examples of the pyrene compound include cascade blue.

Non-limiting examples of the oxazine compound include Nile red, Nile blue, cresyl violet, and oxazine 170.

Non-limiting examples of the acridine compound include proflavin, acridine orange, and acridine yellow.

Non-limiting examples of the arylmethine compound include auramine, crystal violet, and malachite green.

Non-limiting examples of the tetrapyrrole compound include porphin, phtalocyanine, and bilirubin.

Non-limiting examples of the proprietary molecules include CF dye (Biotium), BODIPY (Invitrogen), Alexa Fluor (Invitrogen), DyLight Fluor (Thermo Scientific, Pierce), Atto and Tracy (Sigma Aldrich), FluoProbes (Interchim), DY and MegaStokes Dyes (Dyomics), Sulfo Cy dyes (CYANDYE, LLC), Setau and Square Dyes (SETA BioMedicals), Quasar and Cal Fluor dyes (Biosearch Technologies), SureLight Dyes (APC, RPE, PerCP, Phycobilisomes) (Columbia Biosciences]), APC, APCXL, RPE, and BPE (Phyco-Biotech).

In preferred embodiments, the contrast agents comprises, consists essentially of, or consists of iodine and barium compounds, 5-100 nm iron oxide nanoparticles, nanoparticles or nanorods of platinum, palladium, silver gold and any combination thereof, $^{18}F$-fluorodeoxyglucose, $^{11}C$ (carbon-11), $^{13}N$ (nitrogen-13), $^{15}O$ (oxygen-15), $^{18}F$ (fluorine-18), $^{82}Rb$ (rubidum-82), and any combination thereof.

Embodiment 4: Tumor Sensing

Figure 4:
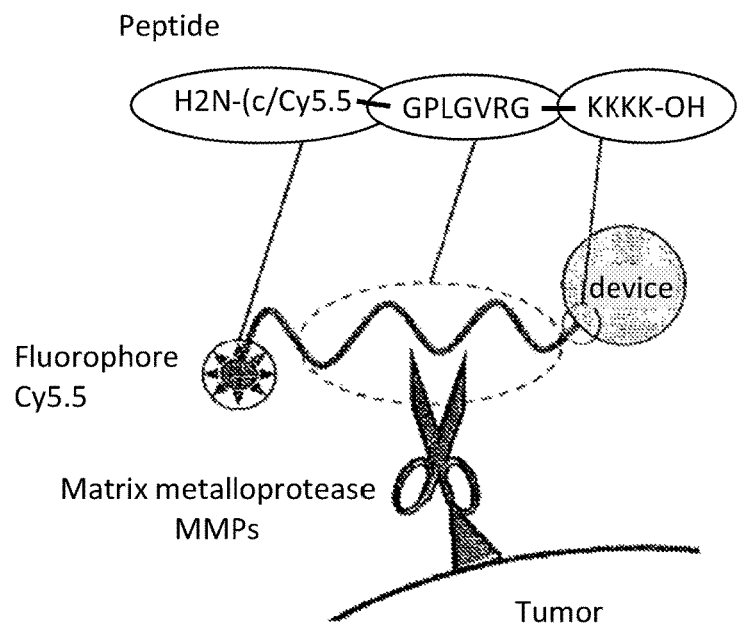
FIG. 4 shows a graphical representation of a tumor sensor.

The fluorophore described above is believed to be linked to a particle that quenches its fluorescence. The link is a peptide bond that can be cleaved specifically by protein specific to target tumors. When the fluorophore-particle assembly is in close vicinity with a tumor, the peptide linker is believed to be severed, separating the fluorophore from the particle, stopping the quenching and fluorescence is recovered, signaling the presence of the tumor. FIG. 4 represents a non-limiting example of this tumor signaling.

Non-limiting examples of the biomarkers are an antibody, a peptide, a guanine nucleotide-binding protein (G protein), and a combination thereof. Non-limiting examples of the antibody includes any glycoprotein belonging to the imunoglobin superfamily. Non-limiting examples of the peptides include any sequence of 50 amino acids or less, not including zero. The amino acids are linked by an amide bond and include dipeptides and tripeptides. Non-limiting examples of the guanine nucleotide-binding protein (G protein) include monomeric small GTPases and heterotrimeric G protein complexes.

Embodiment 5: Therapy

Another embodiment of the present invention relates to therapeutic agents. Non-limiting therapeutic agents include a nucleic acid, a peptide, a protein, a carbohydrate, a fat, a small molecule, and an enzyme that is operable for catalyzing conversion of prodrugs into drugs, metallic nanoparticles, radiation emitting isotopes or combinations thereof. Conjugated Prussian blue nanoparticles can be utilized as photothermal therapy agents in vivo as demonstrated in a neuroblastoma murine model.

In some embodiments, Prussian blue analog lattice compounds, in the form of nanoparticles, are coated with avidin and transferrin selectively target neuroblastoma cells when directly injected into an established mouse flank tumor. Without wishing to be bound to a particular theory, subjecting the tumor to laser photothermal therapy with a near-infrared laser causes the Prussian blue particles to absorb the light and transition from the ground to the excited state, leading to an increase in kinetic energy and heating of the local environment around the light absorbing species. This mechanism heats up the attached cancer cells and induces a hyperthermic effect, ultimately leading to cell ablation and tumor shrinkage in neuroblastoma mice. Tumors were eliminated in 80% of experimental mice and these mice remained tumor free for at least three days after just one treatment.

Figure 5:
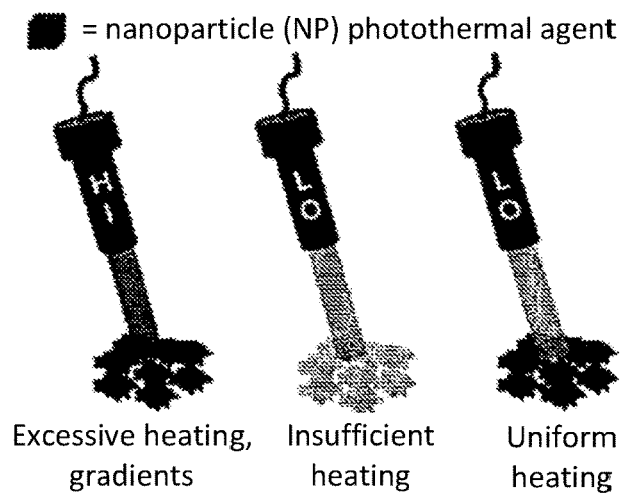
FIG. 5 shows a schematic of laser-induced photothermal therapy (PTT) of tumors.

FIG. 5 illustrates a simplified, non-limiting, representative schematic of laser-induced photothermal therapy (PTT) of tumors. High laser powers result in excessive heating of tumors and temperature gradients (left), while low laser powers result in insufficient heating of tumors (center). NP-based PTT results in uniform tumor heating at low laser powers resulting in efficient tumor ablation (right).

Non-limiting examples therapeutic agents include a nucleic acid, a peptide, a protein, a carbohydrate, a fat, a small molecule, and an enzyme that is operable for catalyzing conversion of prodrugs into drugs, metallic nanoparticles, radiation emitting isotopes.

Non-limiting examples of the nucleic acid include DNA (deoxyribonucleic acid) and RNA (ribonucleic acid), peptide nucleic acid, morpholino-nucleic acid, locked nucleic acid, glycol nucleic acid, and threose nucleic acid.

Non-limiting examples of the peptide include those peptides that comprise, consist essentially of, or consist of 50 amino acids or less, excluding zero, in any sequence thereof, where the sequence of amino acids are linked by an amide bond and include dipeptides and tripeptides.

Non-limiting examples of the proteins include biological molecules consisting of one or more chains of amino acids.

Non-limiting examples of the carbohydrates include monosaccharides, disaccharides, oligosaccharides, and polysaccharides.

Non-limiting examples of the small molecules are organic compounds of less than 1000 Dalton in molecular weight.

Non-limiting examples of the prodrugs include intracellular Type IA, such as Acyclovir, 5-fluorouracil, cyclophosphamide, diethylstilbestrol diphosphate, L-dopa, 6-mercaptopurine, mitomycin C, zidovudine; intracellular Type IB, such as carbamazepine, captopril, carisoprodol, heroin, molsidomine, paliperidone, phenacetin, primidone, psilocybin, sulindac, and fursultiamine; extracellular Type IIA, such as lisdexamfetamine, loperamide oxide, oxyphenisatin, and sulfasalazine; extracellular Type IIB, such as acetylsalicylate, bacampicillin, bambuterol, chloramphenicol succinate, dihydropyridine pralidoxime, dipivefrin, and fosphenytoin; and extracellular Type IIC, such as ADEPTs, GDEPs, and VDEPs.

In preferred embodiments, the metallic nanoparticles are those having a diameter of 5 to 100 nm. Examples include iron oxide nanoparticles having these diameters. The metallic nanoparticles also include nanoparticles or nanorods of platinum, palladium, silver, gold, or a combination thereof.

Non-limiting examples of radiation emitting isotopes include Iodine-131 ($^{131}I$), Lutetium-177 ($^{177}Lu$), Yttrium-90 ($^{90}Y$), Strontium-89 ($^{89}Sr$), and Samarium-153 ($^{153}Sm$).

Embodiment 6: Combination of all of the Above

In another embodiment of the invention, the compositions described above can be used for multimodal imaging or therapy and combinations thereof in subjects or subject-derived specimens. The targeting, imaging and therapeutic agents or combinations thereof are applied to the biocompatible coating by a variety of physical and chemical interactions including, but not limited to, electrostatic (charge-based), covalent, hydrophobic and van der Waal's interactions.

Additional embodiments also relate to methods that comprise, consist essentially of, or consist of treating a subject in need of therapy with a therapeutically effective amount of the composition and/or embodiments described herein. In preferred embodiments, the therapy comprises, consists essentially of, or consists of MRI imaging and/or multimodal imaging, where the compositions described herein are operable as MRI contrasting agents.

Another preferred embodiment relates to methods, which comprise, consist essentially of, or consist of adding a composition described herein to a target, object, a further composition, and/or subject in need of imaging.

Other embodiments include:

1. A composition, comprising a core of doped Prussian blue analog lattice compound comprising interstitial cations and a shell of biocompatible coating modified with a fluorophore, a contrast agent, a targeting agent, a therapeutic agent, or any combination thereof.

2. The composition of embodiment 1, wherein said doped Prussian blue analog lattice compound is represented by general formula (I):

$$A_xB_yM_4[M'(CN)_6]_z \cdot nH_2O \quad (I)$$

wherein:

A represents at least one of $VO_2$, Ca, V, Cr, Mn, Fe, Co, Ni, Cu, Zn, Ga, Sr, Zr, Nb, Li, Na, K, Rb, Cs, Fr, Tl, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

B represents at least one of $VO_2$, Ca, V Cr, Mn, Fe, Co, Ni, Cu, Zn, Ga, Sr, Zr, Nb, Li, Na, K, Rb, Cs, Fr, TI, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

M represents at least one of $VO_2$, Ca, V, Cr, Mn, Fe, Co, Ni, Cu, Zn, Ga, Sr, Zr, Nb, Li, Na, K, Rb, Cs, Fr, TI, Mo, Ru, Rh, Pd, Au, Cd, In, Lu, Ba, Hf, Ta, W, Os, Pt, Hg, La, Eu, Gd, Tb, Dy and Ho, in any oxidation state and any combination thereof;

M' represents at least one of $VO_2$, Ca, V, Cr, Mn, Fe, Co, Ni, Cu, Zn, Ga, Sr, Zr, Nb, Li, Na, K, Rb, Cs, Fr, TI, Mo, Ru, Rh, Pd, Ag, Cd, In, Lu, Ba, Hf, Ta, W, Os, Pt, Hg, La, Eu, Gd, Tb, Dy and Ho, in any oxidation state and any combination thereof;

x is from 0.1 to about 1;
y is from 0.1 to about 1;
z is from 0.1 to about 4; and
n is from 0.1 to about 24.

3. The composition of embodiment 1, wherein said doped Prussian blue analog lattice compound is represented by general formula (I):

$$A_xB_yM_4[M'(CN)_6]_z \cdot nH_2O \quad (I)$$

wherein:

A represents at least one of $VO_2$, Ca, V, Cr, Mn, Fe, Co, Ni, Cu, Zn, Ga, Sr, Zr, Nb, Li, Na, K, Rb, Cs, Fr, TI, Mo, Ru, Rh, Pd, Ag, Cd, In, Lu, Ba, Hf, Ta, W, Os, Pt, Hg, La, Eu, Gd, Tb, Dy and Ho, in any oxidation state;

B represents at least one of Mn, Gd, in any oxidation state and any combination thereof; and each of M and M' represents Fe.

4. The composition of embodiment 1, wherein said doped Prussian blue analog lattice compound is represented by general formula (I):

$$A_xB_yM_4[M'(CN)_6]_z \cdot nH_2O \quad (I)$$

wherein:

A represents K;

B represents Mn and/or Gd, in any oxidation state; and each of M and M' represents Fe.

5. The composition of embodiment 4, wherein said doped Prussian blue analog lattice compound represented by general formula (I) is at least one member selected from the group consisting of $K_{0.53}Gd_{0.89}Fe^{III}_4[Fe^{II}(CN)_6]_{3.8} \cdot 1.2H_2O$ and $K_{0.6}Mn_{0.7}Fe^{III}_4[Fe^{II}(CN)_6]_{3.5} \cdot 3H_2O$.

6. The composition of embodiment 2, wherein said doped Prussian blue analog lattice compound has a particle size of about 1 nanometer to about 10 microns.

7. The composition according to embodiment 1, wherein said biocompatible coating stabilizes the composition against aggregation, serve as a platform for attachment of molecules or metals, and prevent leakage of ions from the core to the surrounding.

8. The composition according to embodiment 1, wherein said imaging is medical radiography, magnetic resonance imaging, scintigraphy, single-photon emission computed tomography, positron emission tomography, photoacoustic imaging, ultrasound, optical fluorescence imaging, optical bioluminescence imaging, surface enhanced Raman scattering imaging, intravital microscopy, or any combination thereof.

9. The composition according to embodiment 1, wherein said biocompatible coating is in contact with the core by physical or chemical interactions between the biocompatible coating and the core.

10. The composition according to embodiment 9, wherein said physical or chemical interactions are electrostatic interactions, covalent interactions, hydrophobic interactions, van dew Waal's interactions, or any combination thereof.

11. An imaging agent comprising the composition according to embodiment 1.

12. A therapeutic agent comprising the composition according to embodiment 1, wherein said contrast agent, targeting agent, or therapeutic agent is present in said photothermally responsive material and has a wavelength absorbance maximum of about 600 nm to 1200 nm.

13. A therapeutic agent comprising the composition according to embodiment 1, a peptide and fluorophore for imaging protease expressed in cell and in tissue.

14. The composition according to embodiment 1, by which a quenching effect is generated with the fluorophore on the surface thereof.

15. A method for diagnosing a subject or target composition with a disorder or disease, comprising administering a therapeutically effective amount of the composition according to embodiment 1 to a subject or target composition in need thereof.

16. A method of imaging a tumor cell in a patient, comprising administering a therapeutically effective amount of the composition according to embodiment 1 to a subject in need thereof.

EXAMPLES

The following examples illustrate embodiments of the present invention. Unless indicated otherwise, the term "GdPB" used in the examples hereinbelow refers to gadolinium-comprising Prussian blue analog lattice compounds. Unless indicated otherwise, the term "MnPB" used in the examples hereinbelow refers to manganese-comprising Prussian blue analog lattice compounds.

Example 1—New Material GdPB $K_xGd_yFe^{III}_4[Fe^{II}(CN)_6]_z \cdot nH_2O$

The species $K_{0.53}Gd_{0.89}Fe^{III}_4[Fe^{II}(CN)_6]_{3.8} \cdot 1.2H_2O$ was obtained by a method described above.

Figure 6:
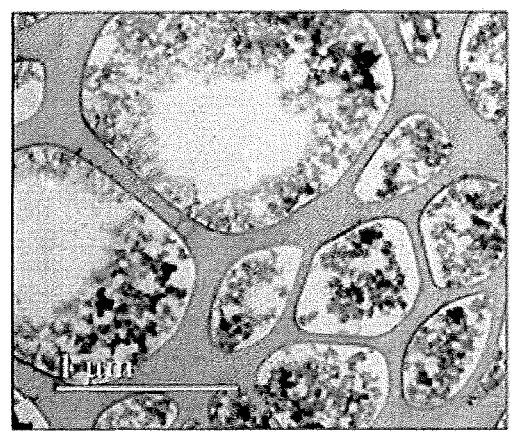
FIG. 6 shows a TEM image of oversized agglomerate consisting of over 1000 nanoparticles.
Figure 7:
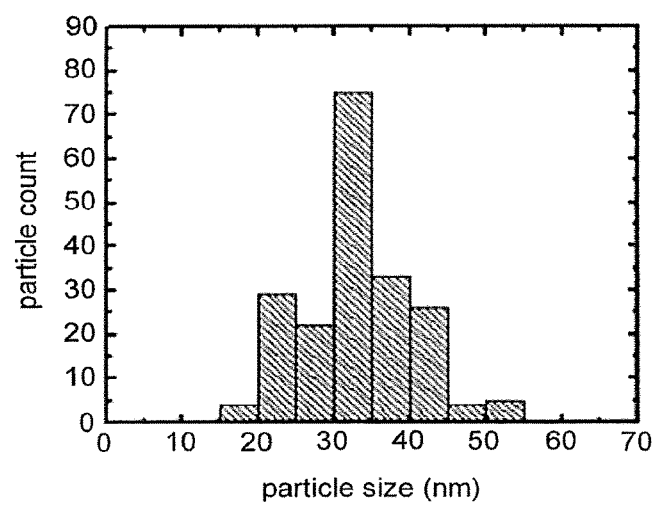
FIG. 7 shows a histogram showing the size distribution of 198 nanoparticles with a mean nanoparticle size of 33 (±7) nm.

The size of the $K_{0.53}Gd_{0.89}Fe^{III}_4[Fe^{II}(CN)_6]_{3.8} \cdot 1.2H_2O$ particles was obtained using by Transmission electron microscopy (TEM). A TEM image of an oversized agglomerate consisting of over 1000 nanoparticles (scale bar=1 μm) used for SAED is provided in FIG. 6. A histogram showing the size distribution of 198 nanoparticles with a mean nanoparticle size of 33 (±7) nm is provided in FIG. 7. The size analysis was performed with Image J imaging software by manually measuring the size of the individual nanoparticles from the TEM images of well dispersed, individual nanoparticles as shown in FIG. 6.

Example 2—New Material GdPB $K_xGd_yFe^{III}_4[Fe^{II}(CN)_6]_z \cdot nH_2O$

Figure 8:
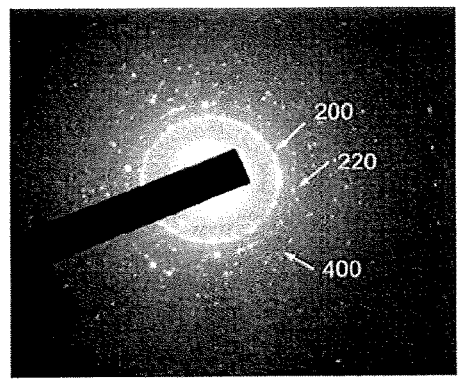
FIG. 8 shows a SAED pattern taken of GdPB.

The size of the $K_{0.53}Gd_{0.89}Fe^{III}_4[Fe^{II}(CN)_6]_{3.8} \cdot 1.2H_2O$ particles were measured by selected area electron diffraction. The SAED pattern taken of GdPB with the 200, 220 and 400 reflections identified as the lattice corresponding to a crystalline compound with a cubic lattice with a lattice parameter of 10.19 Å is show in FIG. 8.

Example 3—New Material GdPB $K_xGd_yFe^{III}_4[Fe^{II}(CN)_6]_z \cdot nH_2O$

We analyzed $K_{0.53}Gd_{0.89}Fe^{III}_4[Fe^{II}(CN)_6]_{3.8} \cdot 1.2H_2O$ using Fourier transform infrared spectroscopy (FTIR) and determined that the material is a coordination polymer containing gadolinium cations ($Gd^{3+}$) contained within the interstitial vacancies (i.e. tetragonal sites of the lattice; GdPB). During synthesis, divalent $Fe^{2+}$ ions react with $[Fe(CN)_6]^{3-}$ to form Prussian blue incorporating $Gd^{3+}$ as interstitial ions. It is also possible for $[Fe(CN)_6]^{3-}$ to react with $Gd^{3+}$ and form the gadolinium hexacyanoferrate Prussian blue analog ($KGd[Fe(CN)_6] \cdot nH_2O$; abbreviated as GdFePBA).

Figure 9:
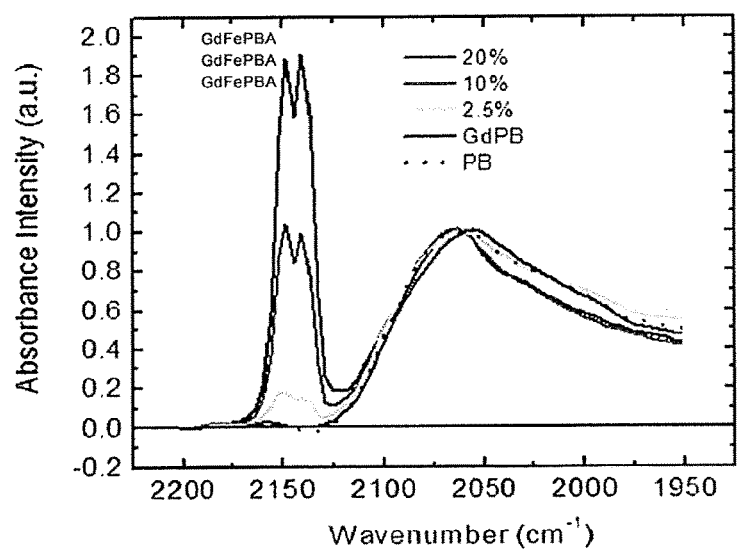
FIG. 9 indicates that GdFePBA is detectable in small quantities when mixed with Prussian blue using FTIR.

In order to verify that there is no formation of GdFePBA during our synthesis of GdPB, various amounts of GdFePBA and Prussian blue were mixed (PB; without interstitial $Gd^{3+}$) to obtain a series of samples containing varying ratios of GdFePBA and PB—20%, 10%, 2.5%, and 0% GdFePBA in a mixture of GdFePBA and PB and acquired FTIR spectra of the resulting powders (varying shades of grey depicting different proportions of GdFePBA) are shown in FIG. 9.

We also measured the FTIR spectra of the GdPB powder (solid blue line) and PB powder (dotted line). The absorption bands corresponding to the cyanide stretching frequencies for PB (broad peak at 2070 $cm^{-1}$), GdPB (broad peak at 2070 $cm^{-1}$), and GdFePBA (double peak at 2145 $cm^{-1}$ and 2155 $cm^{-1}$) were easily resolved. FIG. 9 show the FTIR spectra of GdPB (solid blue line), pure Prussian blue without interstitial gadolinium (dotted line), and Prussian blue mixed with GdFePBA (shades of grey). In the cyanide stretching region (1900 $cm^{-1}$-2300 $cm^{-1}$), GdPB, similar to native Prussian blue (without gadolinium), features a broad band at 2070 $cm^{-1}$ corresponding to the $Fe^{II}$—CN—$Fe^{III}$ cyanide stretch energy. The FTIR spectrum of GdFePBA displays the noticeable double peak pattern at 2145 $cm^{-1}$ and 2155 $cm^{-1}$, typical of gadolinium hexacyanoferrate ($GdFe(CN)_6$).

Figure 10A:
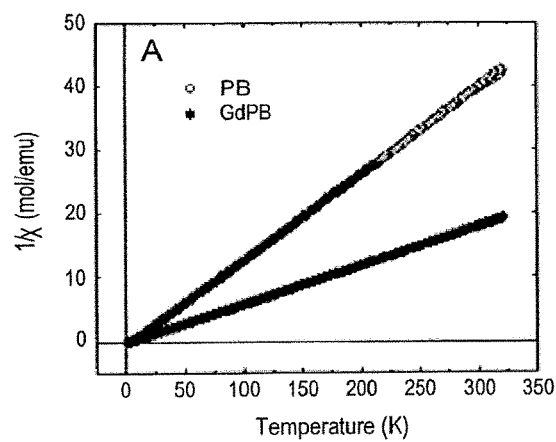
FIGS. 10A and 10B show magnetic measurements of the GdPB and PB nanoparticles obtained by SQUID magnetometry.
Figure 10B:
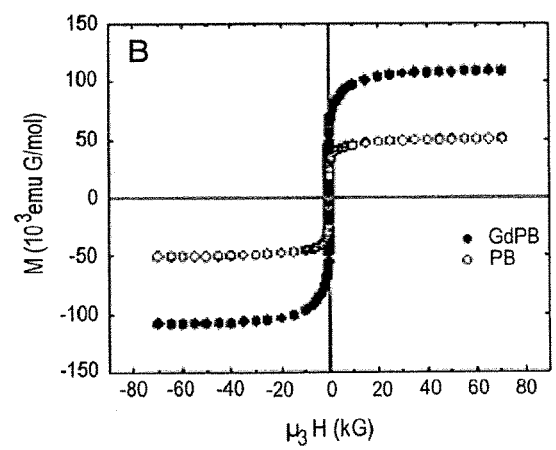

The results shown in FIG. 9 indicate that GdFePBA is detectable in small quantities when mixed with Prussian blue using FTIR (as low as 2.5% GdFePBA in a mixture of GdFePBA and PB). The spectrum corresponding to GdPB (solid blue line) does not feature the double peak observed for GdFePBA suggesting that there is extremely limited formation of Gd FePBA, if any, during the synthesis of GdPB Example 4—New Material GdPB $K_xGd_yFe^{III}_4[Fe^{II}(CN)_6]_z \cdot nH_2O$; SQUID Magnetometry Magnetic measurements of the GdPB and PB nanoparticles were obtained by SQUID magnetometry. FIG. 10A shows the inverse of the susceptibility, $1/\chi$, as a function of temperature at 50 G for GdPB (black circles) and PB (Blue open circles). FIG. 10B shows the isothermal magnetization, M, as a function of field at 1.8 K for GdPB (black circles) and PB (Blue open circles).

Figure 11A:
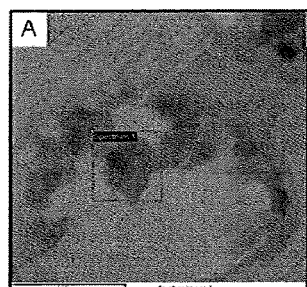
FIGS. 11A and 11B show data related to the composition of the GdPB.
Figure 11B:
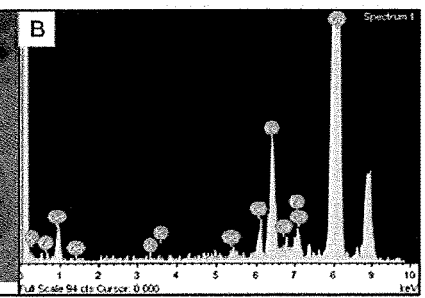

Example 5—New Material GdPB $K_xGd_yFe^{III}_4[Fe^{II}(CN)_6]_z \cdot nH_2O$; Chemical Analysis The composition of the GdPB was determined. FIG. 11A shows a representative TEM image of the GdPB nanoparticles. The purple line indicates the limits of a typical region of interest (ROI) analyzed by EDS. FIG. 11B shows the EDS spectrum corresponding to the ROI shown in FIG. 11A. The composition is derived by the built-in software (INCA, Oxford Instruments, UK) from the attribution of electronic energies profile for Fe, K and Gd.

TABLE E1

Summary of relative percentages of potassium, iron and gadolinium from three distinct EDS scans on GdPB particles.

| | Potassium (%) | Iron (%) | Gadolinium (%) |
|---|---|---|---|
| Spectrum 1 | 0.06 | 88.83 | 11.10 |
| Spectrum 2 | 4.10 | 86.30 | 9.58 |
| Spectrum 3 | 4.03 | 87.23 | 8.72 |

Figure 12B:
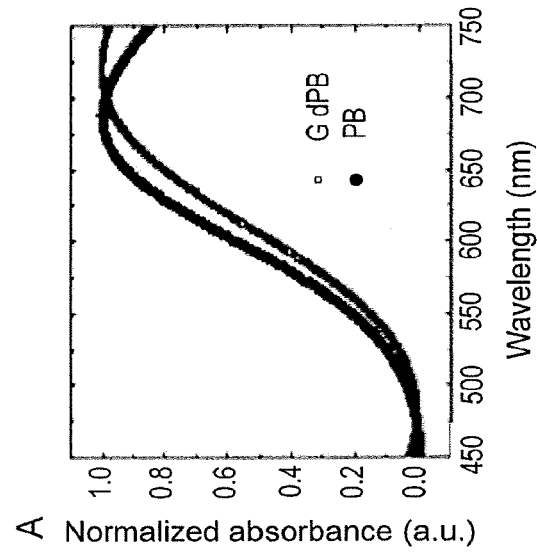
FIGS. 12A and 12B show UV-Vis spectroscopic data for GdPB.
Figure 12A:
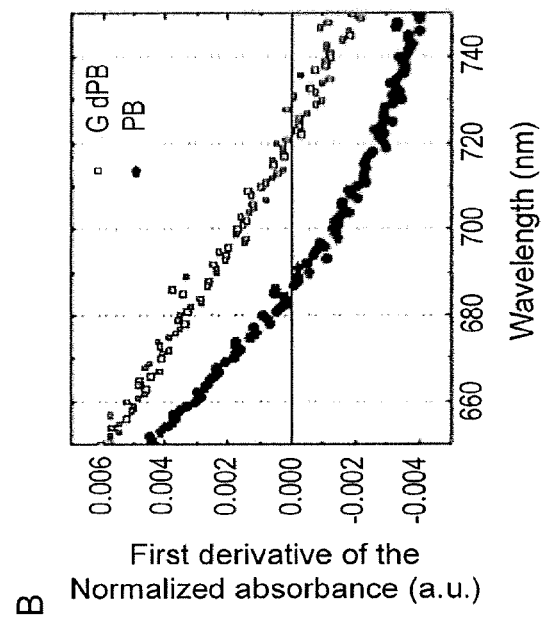

Example 6—New Material GdPB $K_xGd_yFe^{III}_4[Fe^{II}(CN)_6]_z \cdot nH_2O$; UV-Vis Spectroscopy FIG. 12A shows GdPB containing $Gd^{3+}$ in the lattice by UV-Vis spectra of GdPB and PB. FIG. 12B shows the first derivative of the absorbance spectra shown in (A) indicating the redshift for GdPB.

Figure 13:
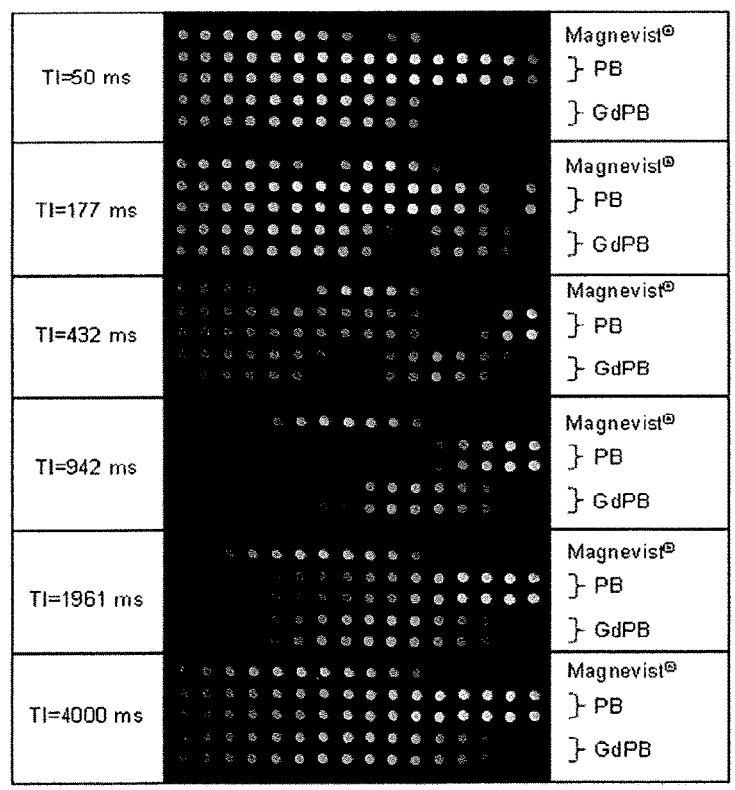
FIG. 13 shows MRI phantoms used for determination of r1 for GdPB.
Figure 14:
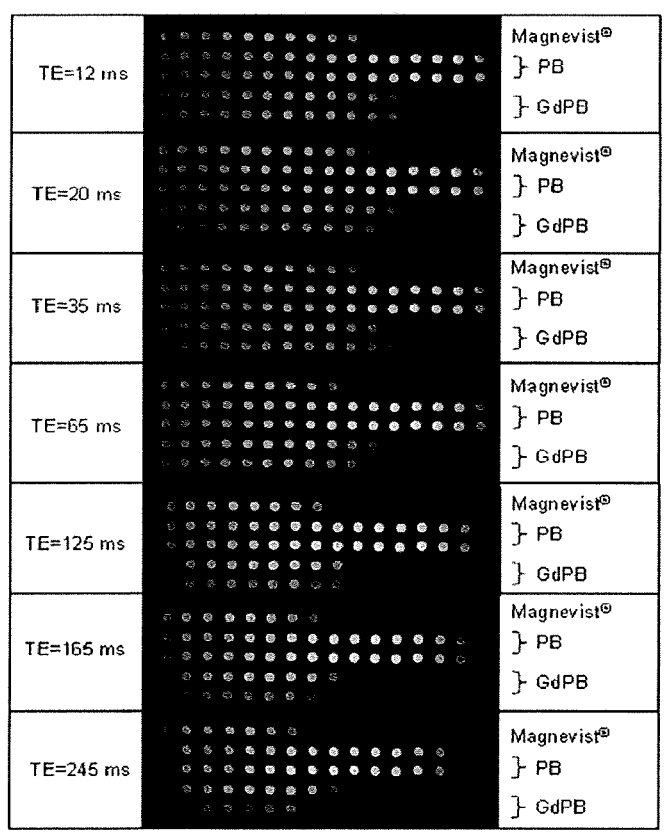
FIG. 14 shows MRI phantoms used for determination of r2 for GdPB.
Figure 15A:
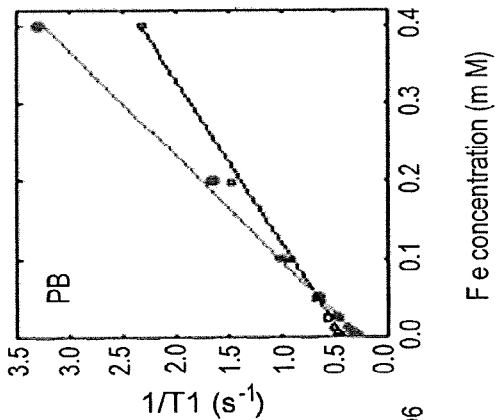
FIGS. 15A, 15B, and 15C show show the inverse of relaxation times plotted against concentrations for GdPB.
Figure 15B:
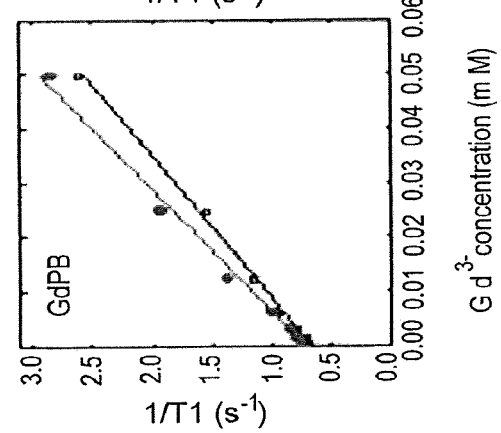
Figure 15C:
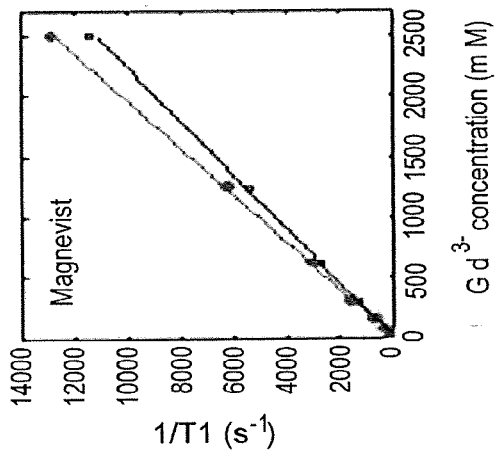

Example 7—New Material GdPB $K_xGd_yFe^{III}_4[Fe^{II}(CN)_6]_z \cdot nH_2O$; MRI Characterization of GdPB: Measurement of r1 and r2 Relaxivities FIG. 13 shows a representative picture of the MRI phantoms used for determination of r1. FIG. 14 shows a representative picture of the MRI phantoms used for determination of r2. FIGS. 15A, 15B, and 15C show the inverse of relaxation time (1/T1=R1 and 1/T2=R2) values plotted against concentrations of main paramagnetic ions. r1 and r2 values are derived from the linear fitting of these plots.

TABLE E2

Calculated values of r1 and r2 in mM−1s−1.

|  | GdPB | | PB | | Magnevist ® | |
|---|---|---|---|---|---|---|
|  | r1 | r2 | r1 | r2 | r1 | r2 |
| Batch 1 | 33.6 | 37.5 | 0.7 | 6.8 | 3.8 | 4.5 |
| Batch 2 | 42.8 | 47.4 | 7.9 | 14.4 | 4.2 | 4.8 |
| Batch 3 | 39.2 | 49.3 | 5.7 | 6.2 | 4.0 | 4.3 |
| Mean | 38.5 | 44.7 | 4.7 | 7.3 | 4.3 | 5.0 |
| Std. dev. | 4.6 | 6.3 | 3.6 | 6.6 | 0.6 | 0.6 |

Example 8—New Material GdPB $K_xGd_yFe^{III}_4[Fe^{II}(CN)_6]_z \cdot nH_2O$; Studies of the Chemical Stability, Cytotoxicity and Colloidal Stability of GdPB Due to the high toxicity of free $Gd^{3+}$ ions, which induces nephrogenic systemic fibrosis in patients with impaired renal function, we titrated aqueous dispersions of GdPB NPs ($5.0 \times 10^{-4}$ M of $Gd^{3+}$) to estimate the amount of free $Gd^{3+}$ present in the suspensions. To this end, xylenol orange was used as a sensitive indicator for the detection of free $Gd^{3+}$ ions as described in the references.

Figure 16:
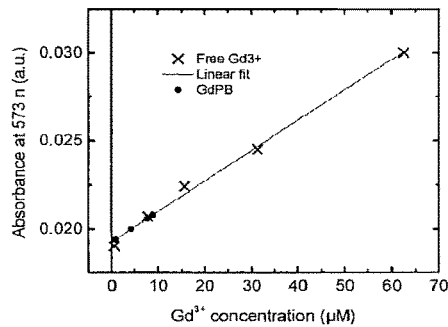
FIG. 16 shows an estimation of free $Gd^{3+}$ present in GdPB NP suspensions using xylenol orange.

FIG. 16 shows an estimation of free $Gd^{3+}$ present in GdPB NP suspensions using xylenol orange. Varying known concentrations of $Gd^{3+}$ were added to a fixed amount of xylenol orange and the resulting absorbances were measured at 573 nm (green crosses indicate the varying known concentrations used and the red line is the resultant linear calibration fit (r2=0.9934). Black circles indicate the concentration of free gadolinium ions observed in the supernatants of 4 distinct batches of GdPB.

From the data shown in FIG. 16, a very low concentration of free $Gd^{3+}$ ions of 5.4±3.6 μM was measured for the 4 batches of GdPB, which include the contributions from residual gadolinium left behind after GdPB synthesis plus minor leakage from the nanoparticles.

To determine significant differences in cell viability for a particular cell type (EoL-1 or OE-21) at a particular time (24 or 48 h), a single-factor ANOVA test was performed. The data were tested to see if they fulfilled the homogeneity of variance assumption.

Additionally, Tukey's tests (multiple comparison tests) were performed to determine which group/groups were significantly different (higher or lower) from other groups within a study (* indicates that the group is significantly different from other groups—higher or lower, p<0.05). The cell viability assay indicates no significant cytotoxicity of the NPs at concentrations lower than $0.5 \times 10^{-6}$ mg/cell after 24 and 48 hours for EoL-1. For OE-21, no significant cytotoxicity was observed for all concentrations investigated at 24 h and no significant cytotoxicity at NP concentrations lower than $0.5 \times 10^{-6}$ mg/cell after 48 hours. The results are shown in FIG. 17.

Figure 17:
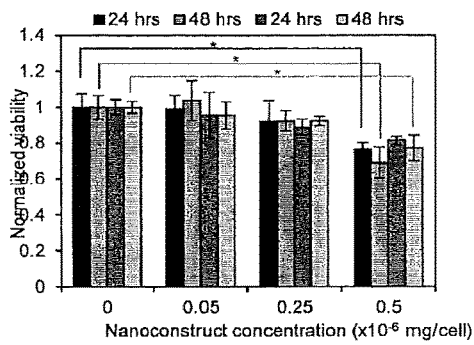
FIG. 17 shows show the cytotoxicity of the biofunctionalized GdPB nanoparticles.

FIG. 17 also shows that the biofunctionalized nanoparticles are not cytotoxic. Viability of the eosinophilic cell line EoL-1 and the squamous epithelial cell line OE-21 co-incubated with varying concentrations of nanoparticles (GdPB-A488-Eot3) determined by the XTT assay. Cells were co-incubated with the nanoparticles for 48 hrs. GdPB-A488-Eot3 is not cytotoxic to EoL-1 at concentrations $<0.5 \times 10^{-6}$ mg/cell at both 24 and 48 h. GdPB-A488-Eot3 is not cytotoxic to OE-21 at all concentrations investigated at 24 h and is not cytotoxic at concentrations $<0.5 \times 10^{-6}$ mg/cell at 48 h (p<0.05).

Figure 18:
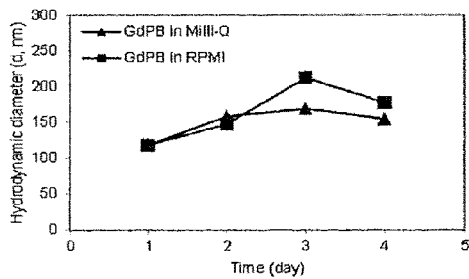
FIG. 18 shows the results of a stability study.

The stability of GdPB in water (Milli-Q) and medium (RPMI 1640; Sigma-Aldrich, St. Louis, Mo., USA) was analyzed for a period of four days post synthesis. FIG. 18 shows the results of a stability study of the GdPB in Milli-Q water and RPMI medium for up to four days post synthesis. The hydrodynamic diameters of GdPB were measured using a Zetasizer Nano ZS (Malvern Instruments, Worcestershire, U.K.).

Figure 19:
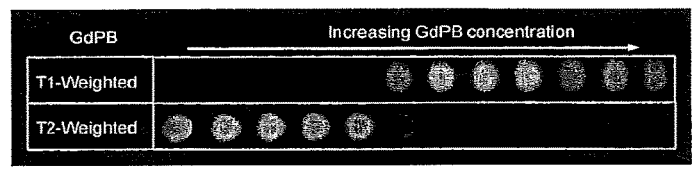
FIG. 19 shows the T1 and T2 weighted MR images at 3T showing hyper and hypo intensity from GdPB.

We took an MRI image of a serial dilution of $K_{0.53}Gd_{0.89}Fe^{III}_4[Fe^{II}(CN)_6]_{3.8} \cdot 1.2H_2O$. We used two different mode of imaging used by radiologist. The first mode is designed to make contrast agent brighter than its environment and gives what is called a T1-weighted pictures, the second mode is designed to make contrast agent darker than its environment and gives a T2-weighted picture. FIG. 19 shows the T1 and T2 weighted MR images at 3T showing hyper and hypo intensity from GdPB.

The relaxivities of $K_{0.53}Gd_{0.89}Fe^{III}_4[Fe^{II}(CN)_6]_{3.8} \cdot 1.2H_2O$ were measured and compared to commercial MRI contrast agents (MAGNEVIST®) and compounds being investigated as MRI contrast agents. The relaxivities (T1 and T2) have been found to be superior to the above-mentioned by an order of magnitude.

TABLE E3

Comparison of the chemical compositions and magnetic characteristics (relaxivities, r1 and r2) of GdPB, Prussian blue and MAGNEVIST ®.

| Contrast agent | Structure a | Chemical composition | Relaxivity (mM−1s−1)b | |
|---|---|---|---|---|
|  |  |  | r1 | r2 |
| GdPB | NP | $K_{0.53}Gd_{0.89}Fe^{III}_4[Fe^{II}(CN)_6]_{3.8} \cdot 1.2H_2O$ | 38.5 ± 4.6 | 44.7. ± 6.3 |
| PB (Prussian blue) | NP | $K_{0.8}Fe^{III}_4[Fe^{II}(CN)_6]_{3.2} \cdot 4.8 \cdot H2O$ | 4.7 ± 3.6 | 7.3 ± 6.6 |
| Magnevist ® | C | $C_{28}H_{54}GdN_6O_{20}$ | 4.3 ± 0.6 | 5.0 ± 0.6 |

Example 9—New Material MnPB $K_xMn_yFe^{III}_4[Fe^{II}(CN)_6] \cdot nH_2O$

FIGS. 20A and 20B show the physical and chemical characterization of the MnPB nanoparticles. FIG. 20A shows a representative TEM images of the MnPB nanoparticles (scale bar=200 nm). FIG. 20B shows a FTIR spectra of MnPB (solid line) and Prussian blue without interstitial manganese (dashed line) in the cyanide stretching region (1900 cm$^{-1}$-2300 cm$^{-1}$). Abbreviations: MnPB, manganese Prussian blue; TEM, transmission electron microscopy; FTIR, Fourier transform infrared spectroscopy.

FIG. 21 shows a T1 and T2 weighted MR images at 3 T showing hyper and hypointensity from PB and MnPB.

Abbreviations: T1W, T1-weighted; T2W, T2-weighted; PB, Prussian blue; MnPB, manganese Prussian blue

TABLE E5

MRI relaxivities of MnPB nanoparticles.

| Contrast agent | Chemical composition | Relaxivity (mM-1s-1) | |
|---|---|---|---|
| | | r1 | r2 |
| MnPB | $K_{0.6}Mn_{0.7}Fe^{III}_4[Fe^{II}(CN)_6]_{3.5} \cdot 3H_2O$ | 15.8 | 143.0 |
| Prussian blue | $K_{2.8}Fe^{III}_4[Fe^{II}(CN)_6]_{3.7} \cdot 2H_2O$ | 7.9 | 14.4 |

Notes: MR measurements of relaxivity were performed at 127 MHz (3 T).
Abbreviations: MnPB, manganese-containing Prussian blue.

Transmission Electron Microscopy (TEM)

FIGS. 22A and 22B show the size of the MnPB nanoparticles. FIG. 22A shows a TEM image of an oversized agglomerate consisting of over 500 nanoparticles (scale bar=1 µm) used for SAED. FIG. 22B shows a histogram showing the size distribution of 198 nanoparticles with a mean nanoparticle size of 33 (±7) nm. The size analysis was performed with Image J imaging software by manually measuring the size of the individual nanoparticles from the TEM images of well dispersed, individual nanoparticles as shown in FIG. 22A.

FIG. 23 shows a SAED pattern taken of MnPB with the 200, 220 and 400 reflections identified as the lattice corresponding to Prussian blue.

Example 10—New Material MnPB $K_xMn_yFe^{III}_4$ $[Fe^{II}(CN)_6].nH_2O$; Energy-Dispersive X-Ray Spectroscopy (EDS)

FIGS. 24A and 24B show images relating to the composition of MnPB. FIG. 24A shows an EDS spectrum corresponding to the region of interest shown in FIG. 24B. FIG. 24B shows a representative TEM image of nanoparticles. The purple line indicates the limits of a typical region of interest analyzed by EDS. The composition was derived by the built-in software (INCA, Oxford Instruments) from the attribution of the electronic energies profile for Fe, K and Mn.

TABLE E4

Summary of relative percentages of potassium, iron and manganese from three distinct EDS scans on MnPB particles.

| | Potassium (%) | Iron (%) | Manganese (%) |
|---|---|---|---|
| Spectrum 1 | 9.03 | 79.86 | 7.86 |
| Spectrum 2 | 8.53 | 85.73 | 7.32 |
| Spectrum 3 | 8.77 | 84.05 | 8.87 |

Example 10—New Material MnPB $K_xMn_yFe^{III}_4$ $[Fe^{II}(CN)_6].nH_2O$; Powder X-Ray Diffraction (XRD)

Figure 25:
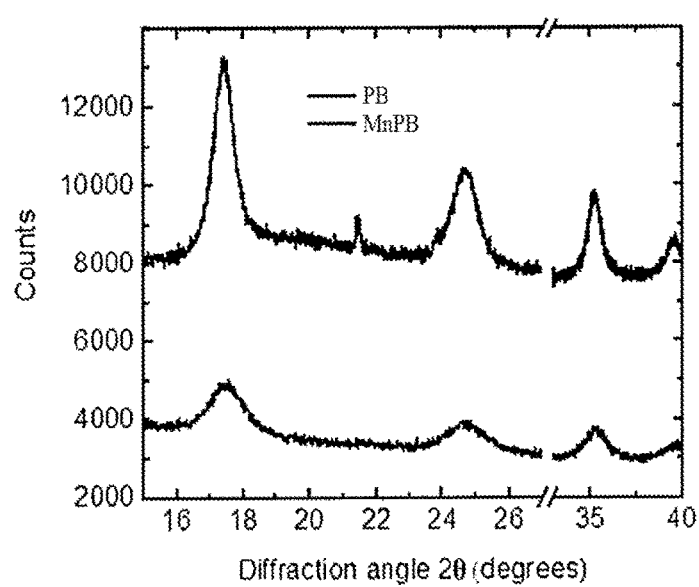
FIG. 25 shows an XRD from a sample of MnPB particles.

FIG. 25 shows a XRD diffractogram from a sample of particles exhibiting several groups of peaks corresponding to the 200, 220 and 400 diffraction planes at 17.43, 24.67 and 35.24 degrees, respectively for MnPB and 17.51, 24.68 and 35.29 degrees respectively for Prussian blue without interstitial manganese (PB). These diffraction peaks were indexed to Prussian blue lattices using the space group Fm-3m (No. 225) and confirmed the presence of one phase constituted by Prussian blue. Using the (400) reflections fitted to a Gaussian function, the lattice parameters for each compound were calculated. We found the following lattice constants: MnPB, a=10.19 Å, and PB, a=10.17 Å. No peaks corresponding to a mixed phase (such Mn as with different lattice parameters were detected, suggesting that both MnPB and PB are made up of the Prussian blue lattice.

Figure 26A:
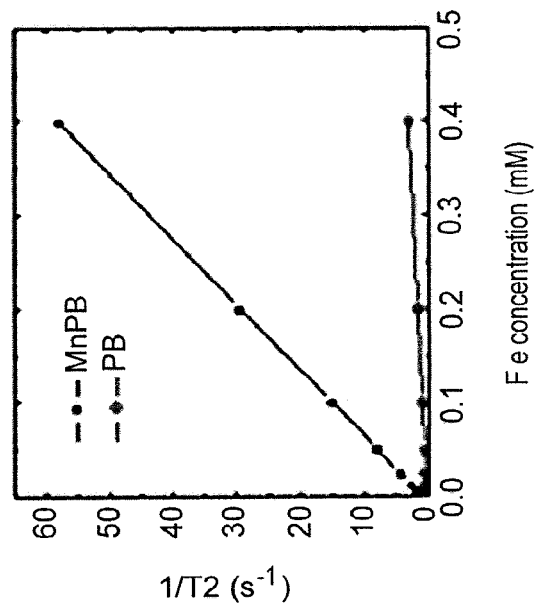
FIGS. 26A and 26B show MR characterization of MnPB.
Figure 26B:
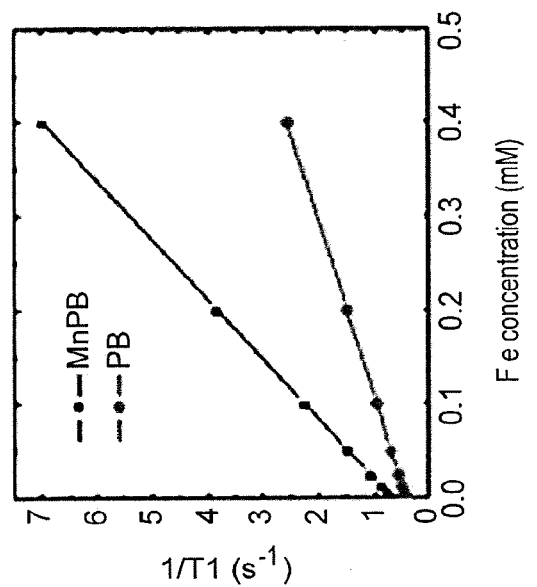

Example 11—New Material MnPB $K_xMn_yFe^{III}_4$ $[Fe^{II}(CN)_6]_z.nH_2O$; MRI Characterization of MnPB: Measurement of r1 and r2 Relaxivities FIGS. 26A and 26B show the inverse of relaxation time (1/T1=R1 and 1/T2=R2) values plotted against concentrations of main paramagnetic ion. r1 and r2 values are derived from the linear fitting of these plots.

Example 12—Biocompatibility and Biomarker Targeting; Cytotoxicity of MnPB

Figure 27A:
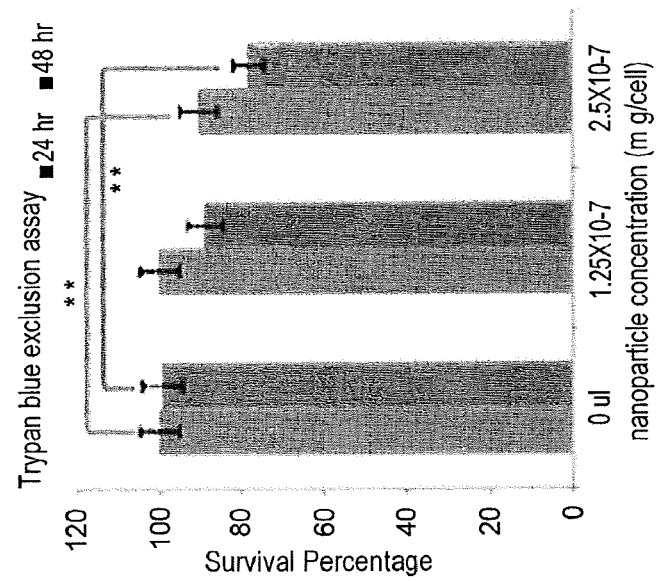
FIGS. 27A and 27B show the cytotoxicity of the biofunctionalized MnPB nanoparticles.
Figure 27B:
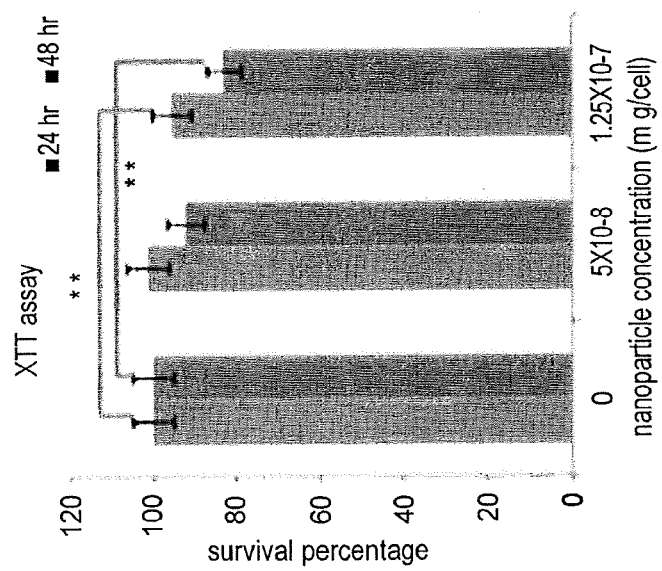

To further assess the safety of the NPs in biological conditions, the cytotoxicity of the biofunctionalized MnPB nanoparticles (i.e. MnPB-A488-ANG2) on BSG D10 cells was investigated. Cytotoxicity was measured by conducting XTT cell viability assays using the cell viability kit supplied by TREVIGEN®. We seeded 10,000 and 50,000 cells per well for BSG D10 respectively in triplicate before adding 0, 0.05, 0.25, 0.5 and 1 (×10-6 mg/cell) of MnPB-A488-ANG2 to the cells. The cells were co-incubated with the nanoparticles for 48 h at 37° C. and 5% $CO_2$. The cell viability assay indicated little to no cytotoxicity of the NPs at concentrations lower than $1.25 \times 10^{-7}$ mg/cell after 24 and 48 hours. The results are show in FIGS. 27A and 27B.

The biofunctionalized nanoparticles are not cytotoxic. Viability of the brain stem glioma cell lines D10 incubated with varying concentrations of nanoparticles (MnPB-A488-ANG2) determined by the XTT assay. Cells were incubated with the nanoparticles for 48 hrs. MnPB-A488-ANG2 was not cytotoxic at concentrations $<1.25 \times 10^{-7}$ mg/cell (** indicates that the group is significantly different from other groups—higher or lower, p<0.05).

Example 13—Biocompatibility and Biomarker Targeting and Flow Cytometry

Figure 28A:
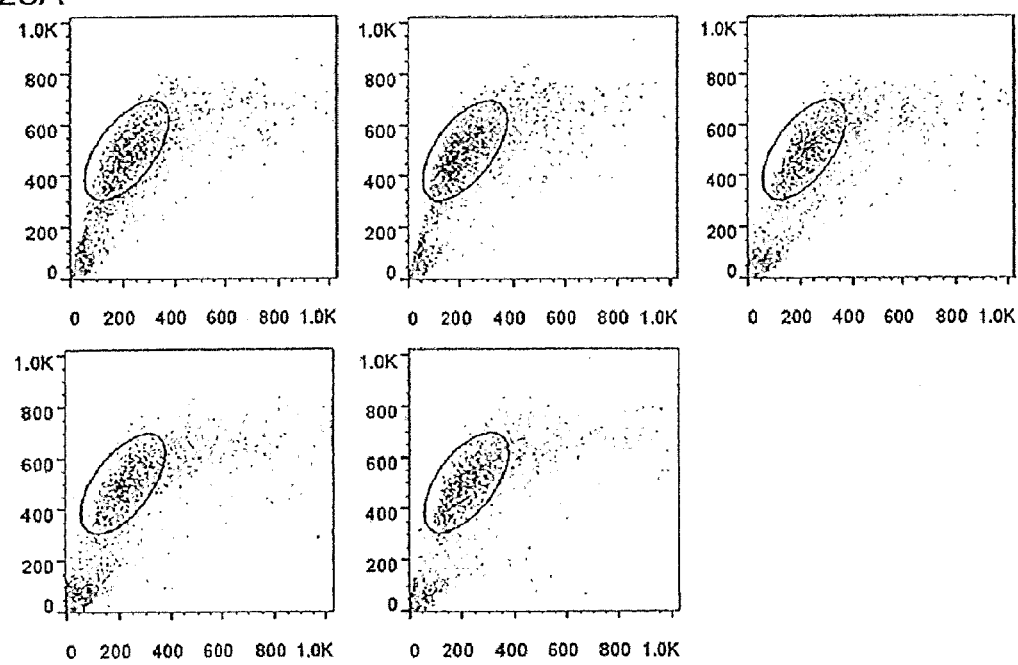
FIGS. 28A, 28B, and 28C show the flow cytometric analysis of nanoparticle specificity.
Figure 28B:
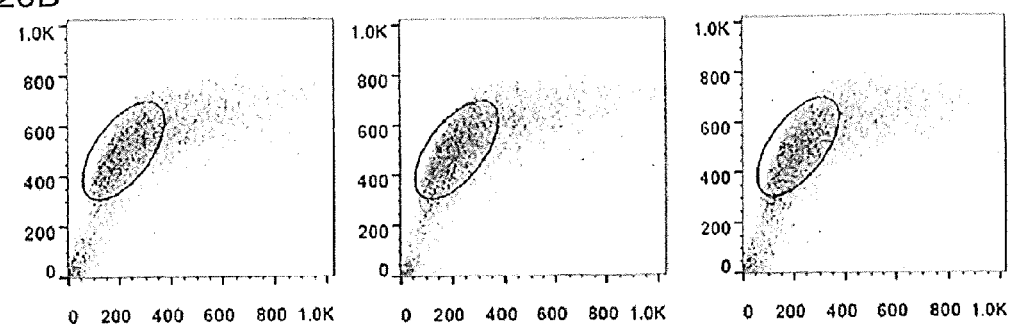
Figure 28C:
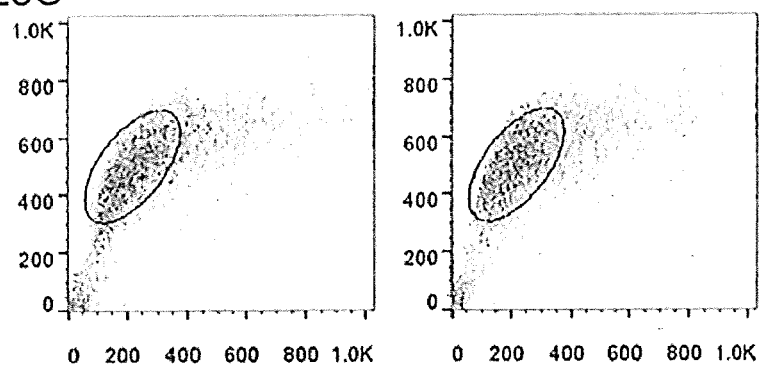

FIGS. 28A, 28B, and 28C show the flow cytometric analysis of nanoparticle specificity. For clarity, the axis legends have been omitted. The side light scattering is displayed on x-axis (abscissa) versus forward light scattering on the y-axis (ordinate). Flow cytometric analysis of the BSG D10 treated in triplicate with (A) MnPB-AV488; (B) MnPB-AV488-AbC and (C) MnPB-A488-ANG2 demonstrated specific targeting of BSG D10 cells using the targeted MnPB-A488-ANG2 nanoparticles.

Figure 29A:
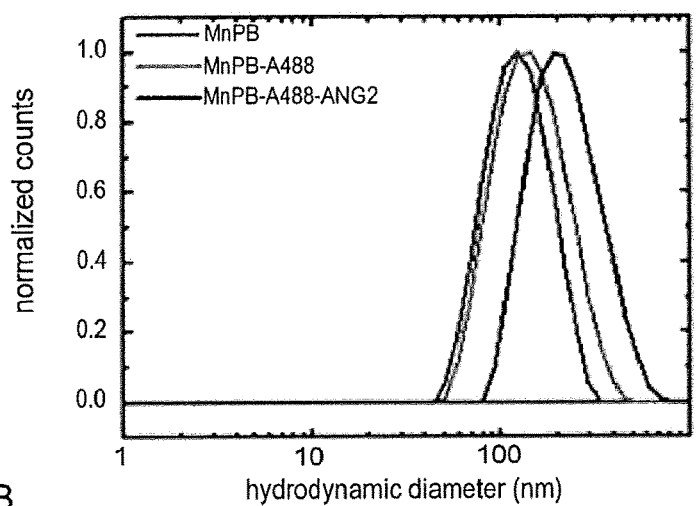
FIGS. 29A and 29B show the size and stability of the biofunctionalized MnPB nanoparticles.
Figure 29B:
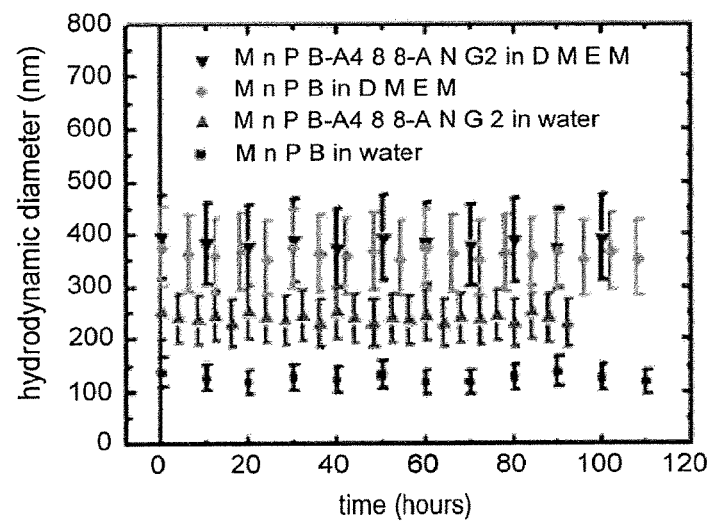

FIGS. 29A and 29B show the size and stability of the biofunctionalized MnPB nanoparticles. FIG. 29A shows the size distributions of the MnPB-A488-ANG2 after each functionalization step. Hydrodynamic size distributions of the MnPB nanoparticles, MnPB nanoparticles coated with avidin-Alexa Fluor 488 (MnPB-A488), and MnPB-A488 modified with biotinylated anti-NG2 (MnPB-A488-ANG2), respectively. FIG. 29B shows the temporal stability of the MnPB and MnPB-A488-ANG2 in Milli-Q water and DMEM medium for up to four days post synthesis. Abbreviations: MnPB, manganese Prussian blue; A488, avidin-Alexa Fluor 488; ANG2, anti-neuron-glia 2 targeting antibody.

Example 14—Multimodal Imaging Composition

Figure 30A:
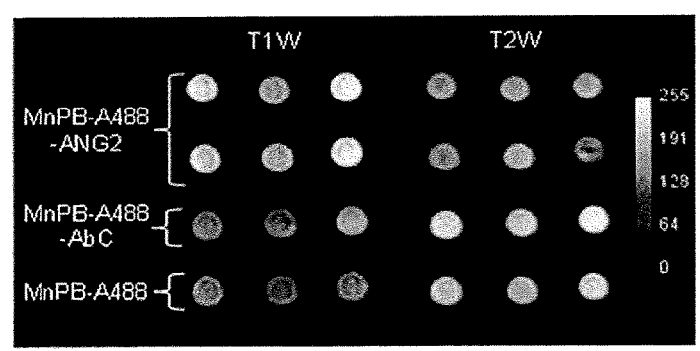
FIGS. 30A and 30B show the molecular MRI-based detection of PBT cells using the biofunctionalized Prussian blue nanoparticles.
Figure 30B:
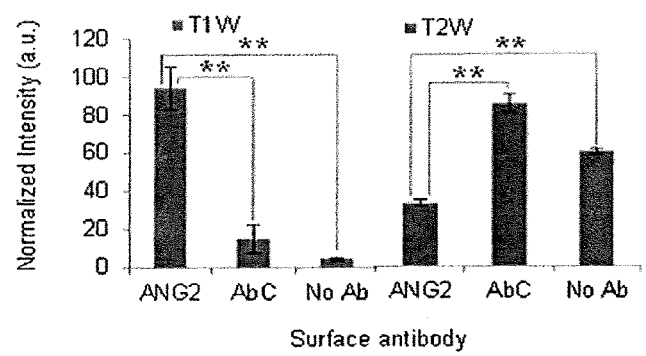

FIGS. 30A and 30B show the molecular MRI-based detection of PBT cells using the biofunctionalized Prussian blue nanoparticles. FIG. 30A shows the T1 and T2 quantitative contrast enhancement in phantoms comprised of a fixed number of the BSG D10 treated with MnPB-A488-ANG2 (ANG2, n=6), MnPB-AV488-AbC (AbC, n=3), and MnPB-AV488 (No Ab, triplicate). FIG. 30B shows the normalized fluorescence signal intensity (a.u.) for BSG D10 treated with ANG2, AbC and no Ab modified MnPB-A488. Abbreviations: MnPB, manganese Prussian blue; A488, avidin-Alexa Fluor 488; ANG2, anti-neuron-glia 2 antibody; AbC, Eotaxin antibody (control).

FIGS. 31A, 31B, and 31C show the fluorescence-based detection of PBT cells using the biofunctionalized Prussian blue nanoparticles. Fluorescent image of BSG D10 treated with control constructs MnPB-A488 (A), MnPB-A488-AbC (B), and MnPB-A488-ANG2 (C). Notes: The green fluorescence comes from A488 on the constructs. Abbreviations: MnPB, manganese Prussian blue; A488, avidin-Alexa Fluor 488; ANG2, anti-neuron-glia 2 antibody; AbC, Eotaxin antibody (control).

FIGS. 32A and 32B show the flow cytometric analysis of the specificity of the biofunctionalized MnPB for PBT cells. FIG. 32A shows a representative histograms of the cell count plotted against Alexa 488 detection levels for BSG D10 cells that are treated with MnPB-AV488 (no Ab, red line), MnPB-AV488-AbC (AbC, blue line), and MnPB-A488-ANG2 (ANG2, black line). FIG. 32B shows a percentage Alexa 488 positive cells (fluorescence intensity cut-off=50) cells for BSG D10 treated with MnPB-A488-ANG2, MnPB-A488-AbC, and MnPB-A488.

Abbreviations: 7-AAD, 7-aminoactinomycin D; MnPB, manganese Prussian blue; A488, avidin-Alexa Fluor 488; ANG2, anti-neuron-glia 2 antibody.

FIGS. 33A, 33B, and 33C show the in vivo fluorescence imaging of nanoparticles in an orthotopic mouse model of PBTs. FIG. 33A shows the fluorescent signal observed in the brains of 5 separate mice with PBTs injected with nanoparticles (tail-vein injection) demonstrating circulation of the nanoparticles through the brain vasculature between 1 and 3 h. Little-no fluorescence is observed at the 6 h and 24 h time-points and controls. FIG. 33B shows a representative ex-vivo fluorescent imaging 3 h post-injection. FIG. 33C shows a histogram representing the biodistribution of the nanoparticles 3 h post-injection demonstrating clearance of the nanoparticles primarily via the liver.

FIGS. 34A, 34B, 34C, and 34D show a histological analysis of the fluorescence positive regions of the mice brains with PBTs. FIG. 34A shows a sagittal slice of mouse brain stained with H&E. FIG. 34A shows an inset showing on the fluorescence image of the brain, a dashed line indicating the position of the slice in shown in FIG. 34A. FIGS. 34C and 34D show progressive zooms of the H&E stained brain sagittal sections containing a hypercellular ventricular and peri-ventricular region within the fluorescence positive region, respectively.

Example 15—Tumor Sensor

FIG. 35 shows a value of the fluorescence intensity of Cy5.5 before and after addition of variable amount of quenching coordination polymer particle.

Example 16—Photothermal Therapy Contains

Figures 36A, 36B:
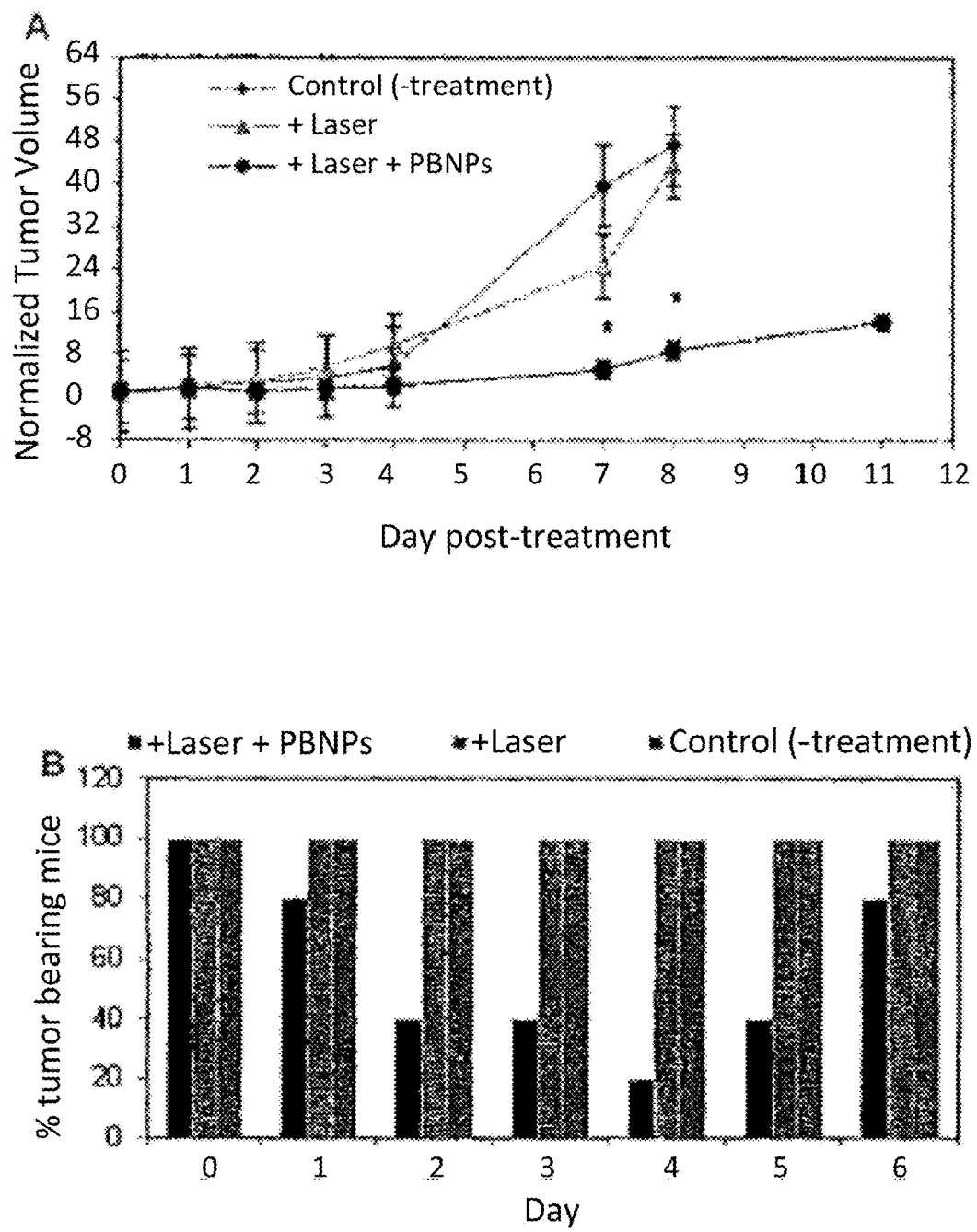
FIGS. 36A and 36B show graphical representation of photothermal therapy results and statistics.

FIGS. 36A and 36B show graphical representation of photothermal therapy results and statistics. FIG. 36A shows normalized tumor volume showing reduction in tumor volume in treated mice (Group 1) relative to untreated mice (Groups 2 and 3). FIG. 36B shows percentage of tumor bearing mice decreases to 20% in Group 1 (+Laser+PB NPs) by day 4 post-treatment, while those in the other groups remain at 100%. *p<0.05

FIG. 37 show results for mice from Group 1, Group 2, and Group 3 after 8 days post-treatment (Top). Tumors from each group were extracted, sectioned, and stained with H&E (Bottom).

We claim:
1. A composition, comprising a core of doped Prussian blue analog lattice compound comprising interstitial cations and a shell of biocompatible coating modified with a fluorophore, a contrast agent, a targeting agent, a therapeutic agent, or any combination thereof; wherein said doped Prussian blue analog lattice compound is represented by general formula (I):

$$A_xB_yM_4[M'(CN)_6]_z \cdot nH_2O \qquad (I)$$

wherein:
x is from 0.1 to 1;
y is from 0.1 to 1;
z is from 0.1 to 4; and
n is from 0.1 to 24;
wherein the Prussian blue analog lattice compound is represented by general formula (I) comprising (i) A is selected from the group consisting of at least one of K, Gd, Mn and Fe; B is a mixture of Mn and Gd, and M and M' are selected from the group consisting of at least one of K, Gd, Mn and Fe; and/or (ii) wherein A is selected from the group consisting of at least one of Li, Na, K, Rb, Cs, and Fr; B is a mixture of Mn and Gd, and M and M' are selected from the group consisting of at least one of Fe, Co, and Ni or mixtures thereof; and/or (iii) wherein A is K and B is a mixture of Mn and Gd, and wherein M and M' are Fe.

2. The composition of claim 1, wherein said doped Prussian blue analog lattice compound has a particle size of about 1 nanometer to about 10 microns.

3. The composition according to claim 1, wherein said biocompatible coating stabilizes the composition against aggregation, serve as a platform for attachment of molecules or metals, and prevent leakage of ions from the core to the surrounding.

4. The composition according to claim 1 in a form suitable for medical radiography, magnetic resonance imaging, scintigraphy, single-photon emission computed tomography, positron emission tomography, photoacoustic imaging, ultrasound, optical fluorescence imaging, optical bioluminescence imaging, surface enhanced Raman scattering imaging, intravital microscopy, or any combination thereof.

5. The composition according to claim 1, wherein said biocompatible coating is in contact with the core by physical or chemical interactions between the biocompatible coating and the core.

6. The composition according to claim 5, wherein said physical or chemical interactions are electrostatic interactions, covalent interactions, hydrophobic interactions, van dew Waal's interactions, or any combination thereof.

7. An imaging agent comprising the composition according to claim 1.

8. A therapeutic agent comprising the composition according to claim 1, wherein said contrast agent, targeting agent, or therapeutic agent is present in said photothermally responsive material and has a wavelength absorbance maximum of about 600 nm to 1200 nm.

9. A therapeutic agent comprising the composition according to claim 1, a peptide and fluorophore for imaging protease expressed in cell and in tissue.

10. The composition according to claim 1, by which a quenching effect is generated with the fluorophore on the surface thereof.

11. A method for detecting a target associated with a disorder or disease, comprising contacting the target with a composition according to claim 1 that interacts with the target, and imaging and detecting the target.

12. The method of claim 11, wherein the target is a cancer cell in a patient and the composition interacts with the cancer cell, thereby imaging and detecting the cancer cell.

13. The composition of claim 1, wherein x, y and z each range from 0.5 to 0.6.

\* \* \* \* \*